(12) United States Patent
Manzi

(10) Patent No.: US 9,336,479 B2
(45) Date of Patent: May 10, 2016

(54) PORTABLE OBJECT AND INFORMATION TRANSMISSION SYSTEM

(71) Applicant: ams AG, Unterpremstaetten (AT)

(72) Inventor: Giuliano Manzi, Graz (AT)

(73) Assignee: ams AG, Unterpremst aetten (AT)

(*) Notice: Subject to any disclaimer, the term of this patent is extended or adjusted under 35 U.S.C. 154(b) by 0 days.

(21) Appl. No.: 14/389,353

(22) PCT Filed: Mar. 19, 2013

(86) PCT No.: PCT/EP2013/055722
§ 371 (c)(1),
(2) Date: Sep. 29, 2014

(87) PCT Pub. No.: WO2013/143923
PCT Pub. Date: Oct. 3, 2013

(65) Prior Publication Data
US 2015/0294215 A1 Oct. 15, 2015

(30) Foreign Application Priority Data
Mar. 30, 2012 (EP) .................................... 12162514

(51) Int. Cl.
*G06K 7/00* (2006.01)
*G06K 19/077* (2006.01)
(Continued)

(52) U.S. Cl.
CPC ........ *G06K 19/07788* (2013.01); *G06K 7/0008* (2013.01); *G06K 7/08* (2013.01);
(Continued)

(58) Field of Classification Search
CPC ....... H01Q 1/2225; H01Q 1/38; H01Q 9/285; H01Q 7/00; H01Q 1/40; H01Q 1/48; H01Q 21/28; H01Q 9/24; H01Q 13/10; H01Q 13/106; H01Q 13/16; H01Q 17/001; H01Q 19/06; H01Q 19/062; H01Q 19/28; G06K 19/07749; G06K 7/0095; G06K 7/0008; G06K 7/10465; G06K 19/077; G06K 19/07756; G06K 19/07786; G06K 19/0723; G06K 19/07747; G06K 19/07767; G06K 19/07769; G06K 19/07783; G06K 19/025; H01L 2224/45015; H01L 2924/20758; H01L 2924/0002; H01L 2924/00; H01L 27/14659; G01R 31/312; G01R 31/2822; G01R 31/3025
USPC .......................................... 235/439, 492, 488
See application file for complete search history.

(56) References Cited

U.S. PATENT DOCUMENTS 6,018,299 A   1/2000  Eberhardt
6,384,727 B1 * 5/2002  Diprizio ............... G06K 19/077
                                                              29/846
(Continued)

FOREIGN PATENT DOCUMENTS

DE    20121494 U1   10/2002
DE    10343546 A1    9/2005
(Continued)

OTHER PUBLICATIONS

Dib, Nihad I. et al.: "Theoretical Characterization of Coplanar Waveguide Transmission Lines and Discontinuities", Nov. 1992, p. 4.

(Continued)

*Primary Examiner* — Thien M Le
(74) *Attorney, Agent, or Firm* — McDermott Will & Emery LLP

(57) ABSTRACT

A portable object (10) comprises an integrated circuit (11), a first pad (12) that is mechanically and electrically connected to the integrated circuit (11) and a second pad (13) that is mechanically and electrically connected to the integrated circuit (11). The portable object (10) is designed for data transfer by capacitive coupling of the first pad (12) to a first conducting line (33) and of the second pad (13) to a second conducting line (34), when the portable object (10) is brought in vicinity to the first and the second conducting line (33, 34).

18 Claims, 19 Drawing Sheets

(51) Int. Cl.
*G06K 7/08* (2006.01)
*G06K 19/07* (2006.01)
*H01Q 1/22* (2006.01)
*H01Q 1/44* (2006.01)
*H01Q 9/28* (2006.01)

(52) U.S. Cl.
CPC ............ *G06K 7/081* (2013.01); *G06K 19/077* (2013.01); *G06K 19/0723* (2013.01); *G06K 19/07756* (2013.01); *H01Q 1/2225* (2013.01); *H01Q 1/44* (2013.01); *H01Q 9/285* (2013.01)

(56) References Cited

U.S. PATENT DOCUMENTS

| | | | |
|---|---|---|---|
| 6,879,809 | B1 | 4/2005 | Vega et al. |
| 7,551,141 | B1 | 6/2009 | Hadley et al. |
| 7,845,375 | B2 | 12/2010 | Dorney |
| 2004/0160233 | A1* | 8/2004 | Forster ............... G06K 7/0008 324/667 |
| 2004/0195319 | A1 | 10/2004 | Forster |
| 2005/0052283 | A1 | 3/2005 | Collins et al. |
| 2006/0059964 | A1* | 3/2006 | Bass .................. A45C 11/321 70/408 |
| 2006/0214869 | A1* | 9/2006 | Kuroda ................. H01Q 1/38 343/846 |
| 2006/0226982 | A1 | 10/2006 | Forster |
| 2011/0109442 | A1* | 5/2011 | Pavlov ................ G06K 7/0008 340/10.4 |
| 2011/0114647 | A1 | 5/2011 | Hallberg |
| 2012/0019417 | A1 | 1/2012 | Manzi et al. |

FOREIGN PATENT DOCUMENTS

| | | |
|---|---|---|
| DE | 102010028926 A1 | 11/2011 |
| EP | 1890271 A1 | 2/2008 |
| FR | 2912124 A1 | 8/2008 |
| WO | WO-2007003247 A1 | 1/2007 |

OTHER PUBLICATIONS

Wadell, Brian C.: "Transmission Line Design Handbook", 1991 Artech House Inc., ISBN 0-89006-436-9, pp. 82-87.

* cited by examiner

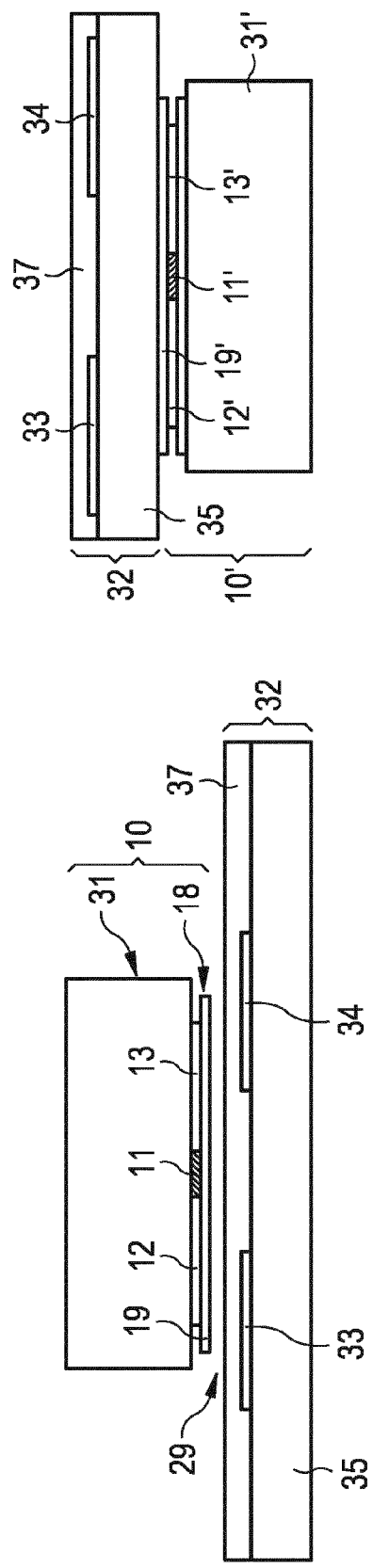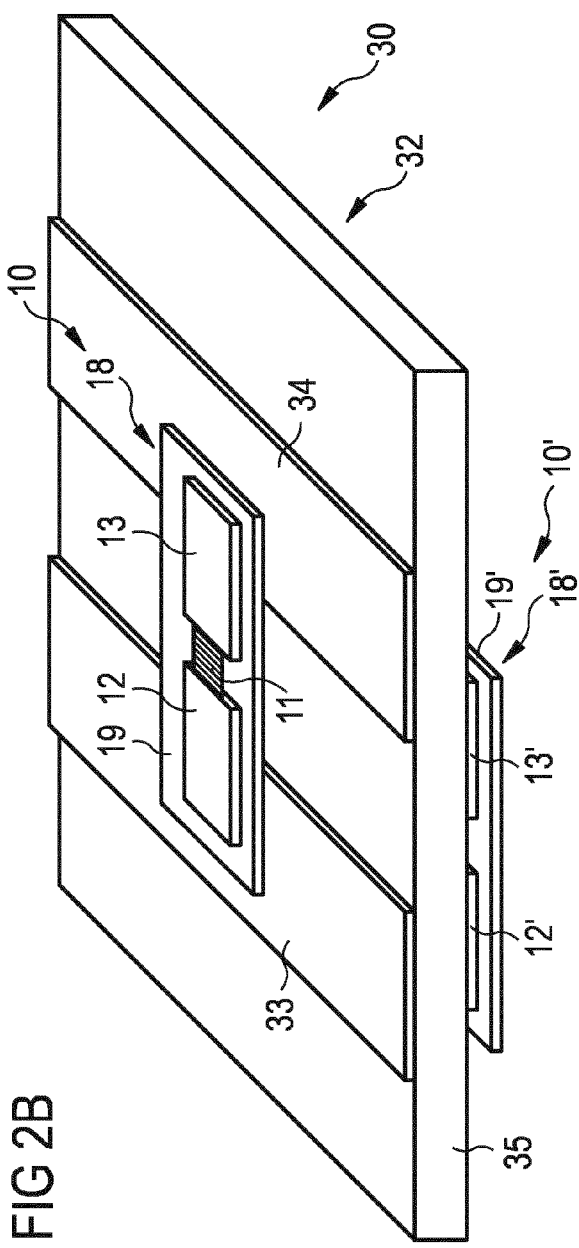
FIG 2B

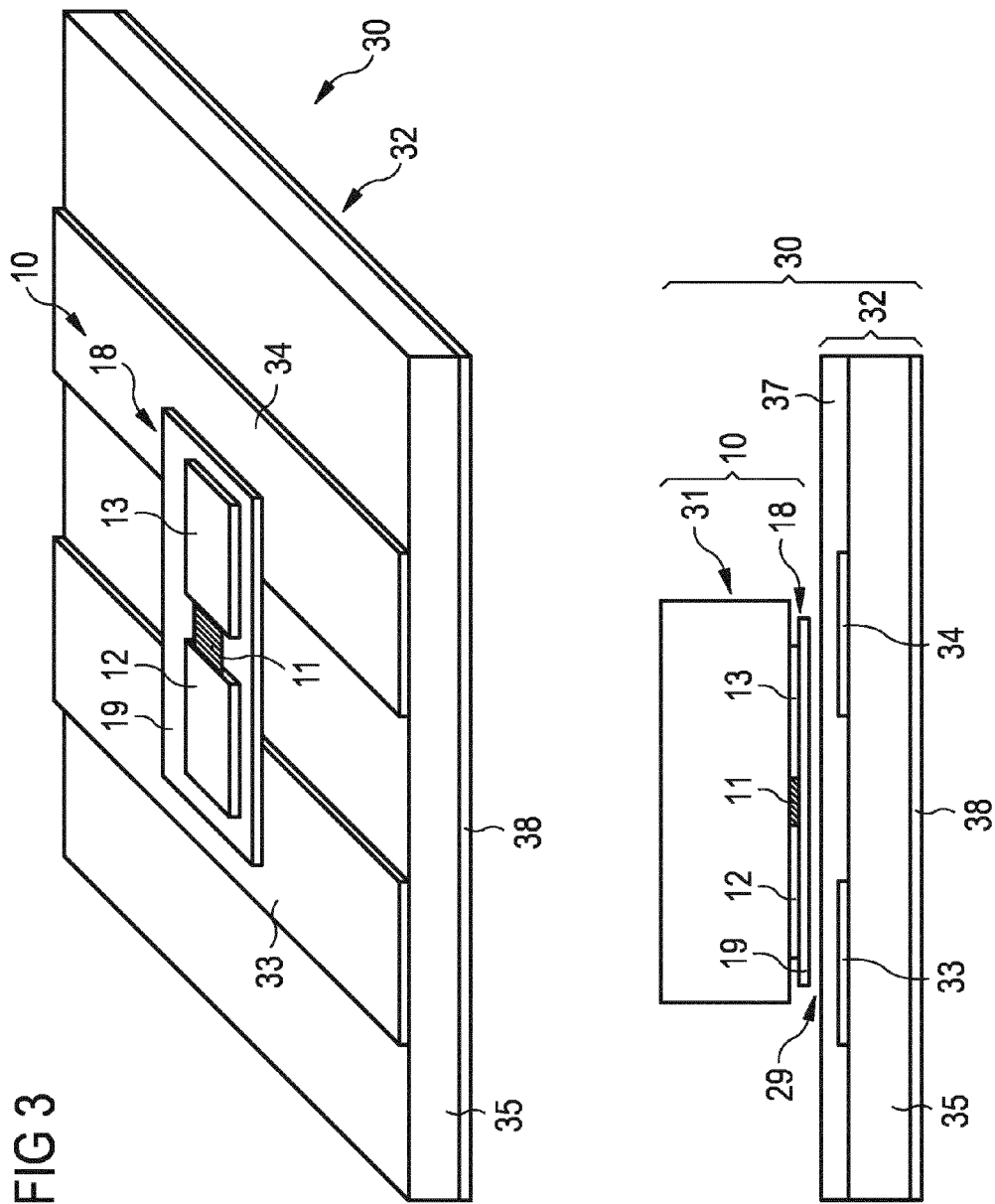

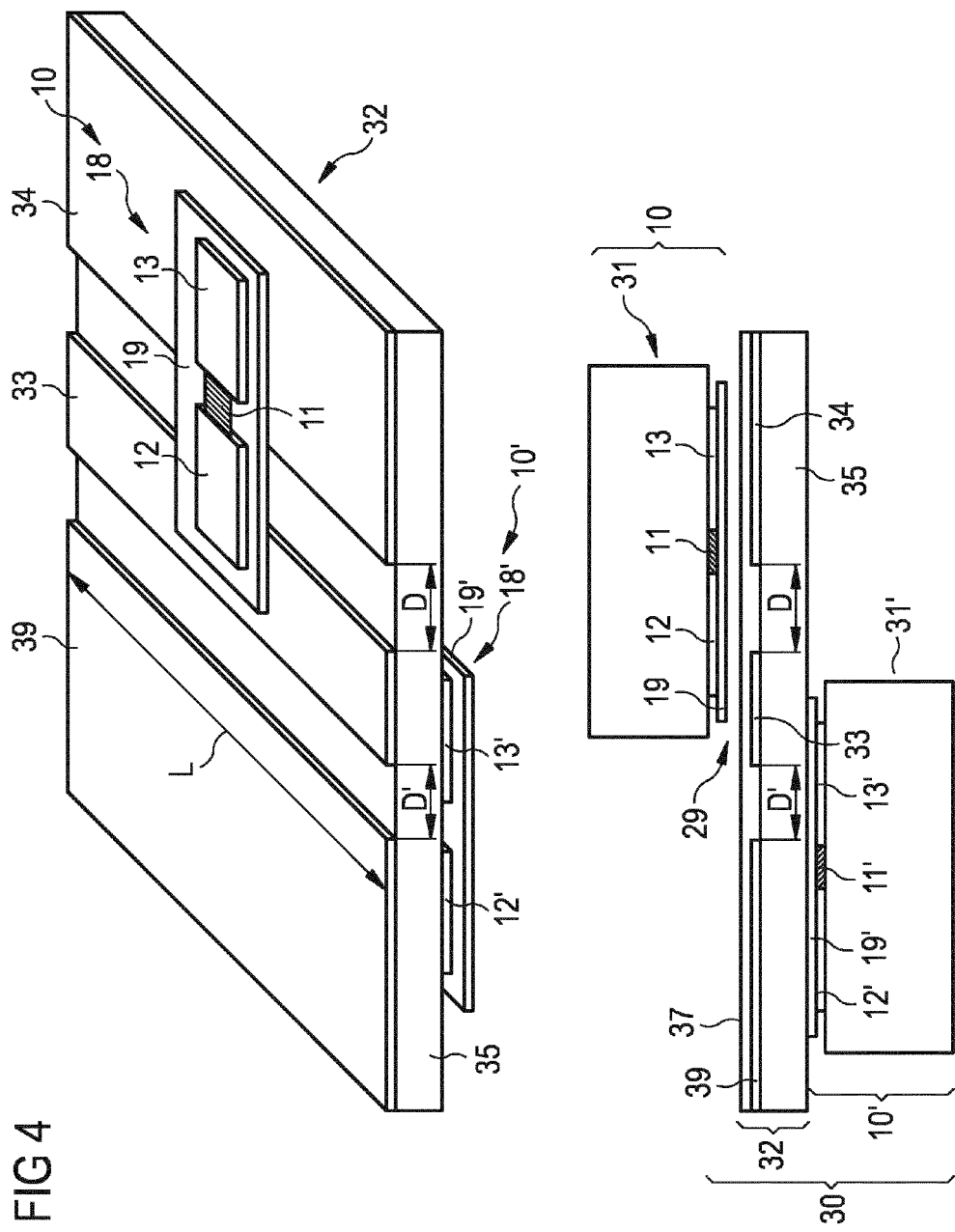

FIG 6
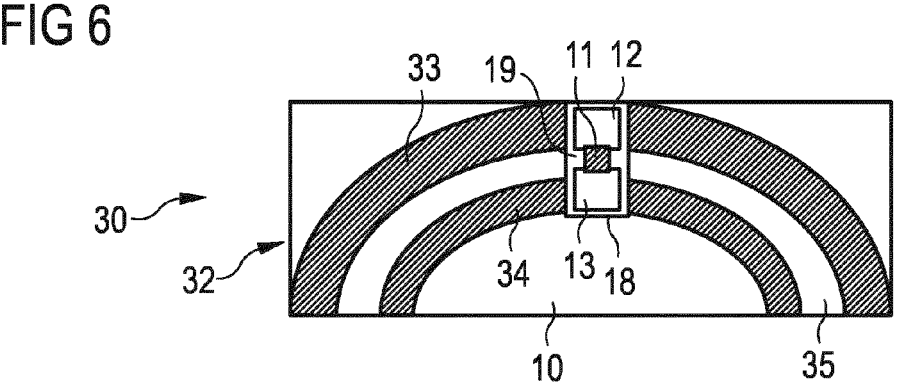
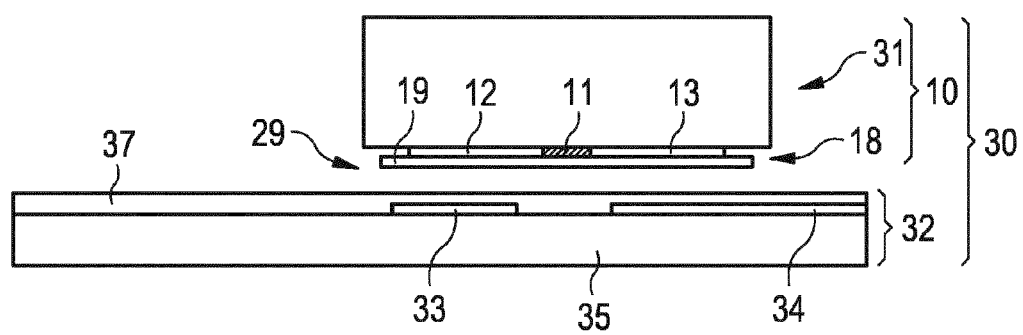

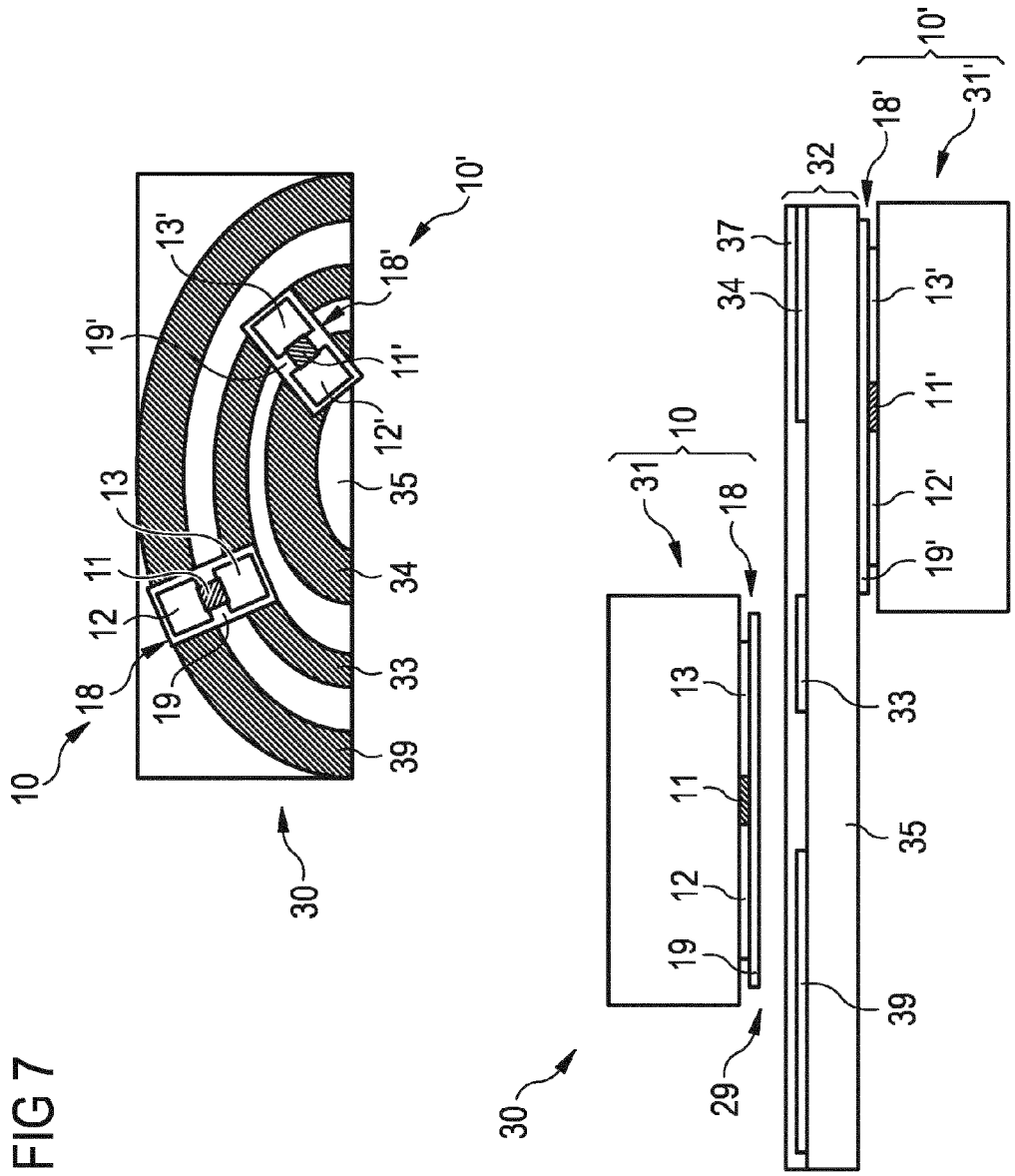

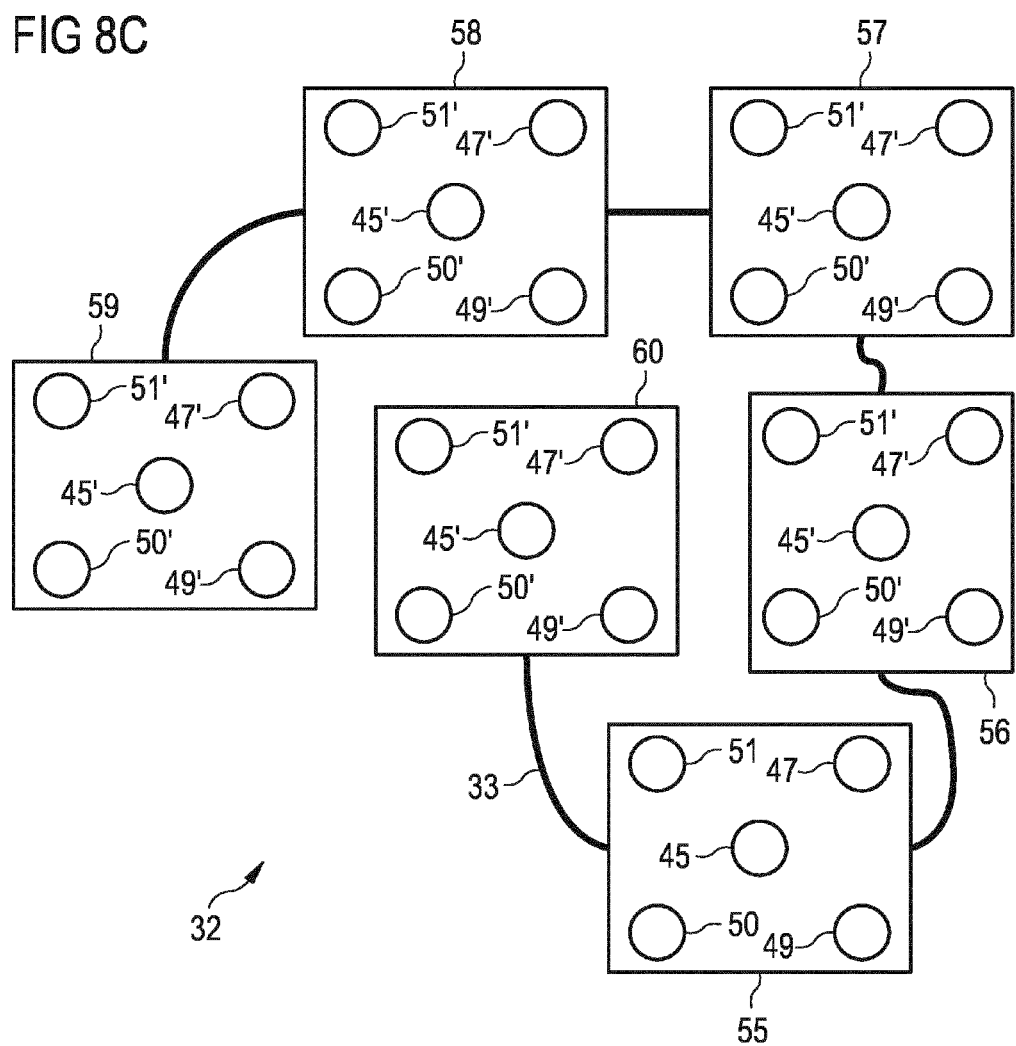

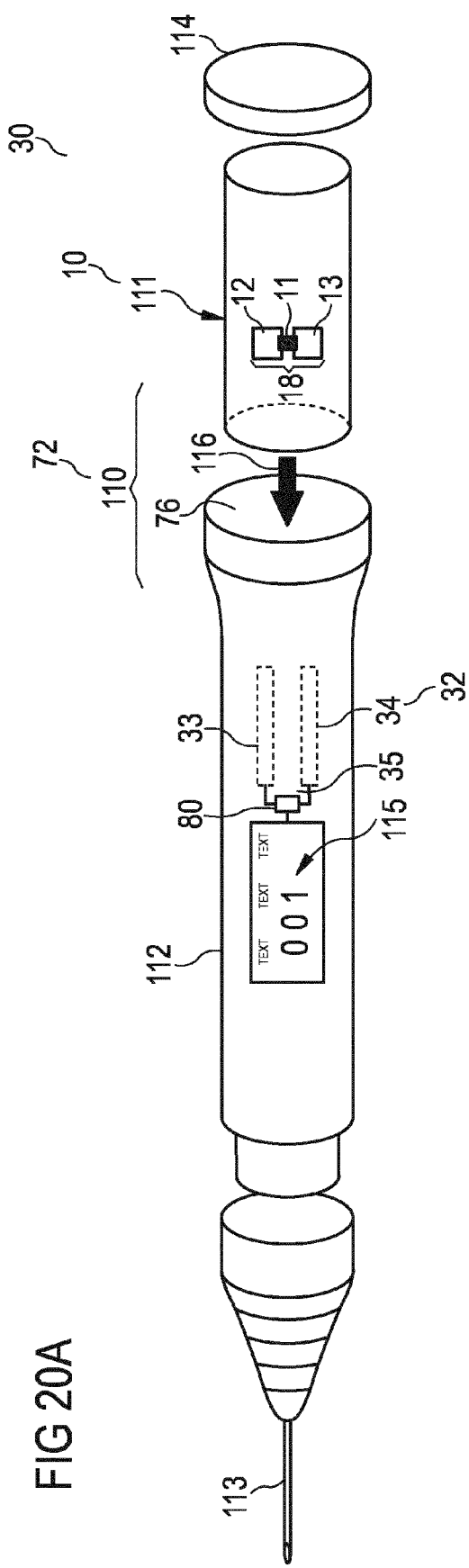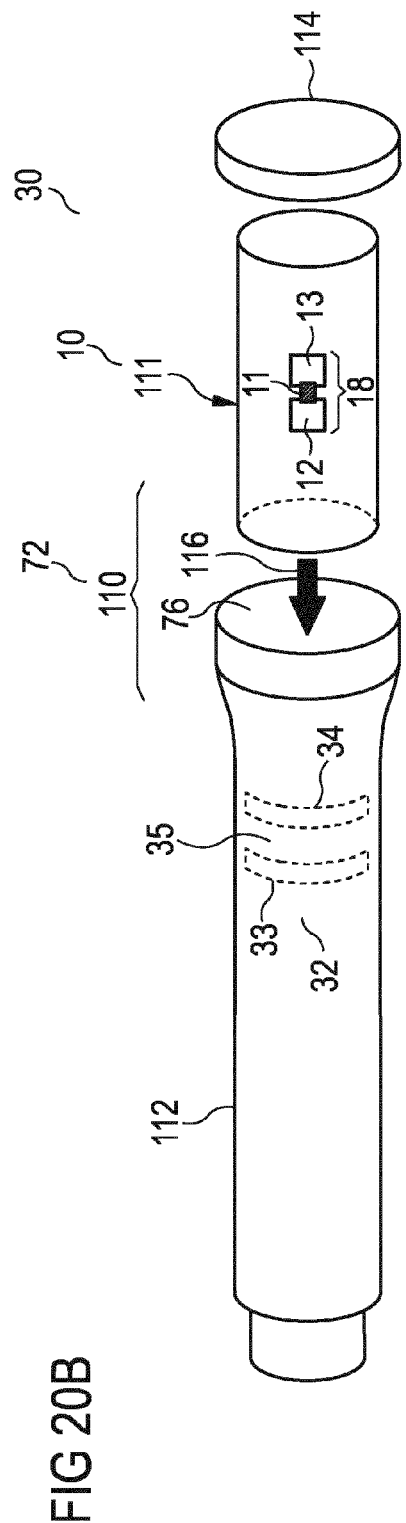
FIG 20A
FIG 20B

PORTABLE OBJECT AND INFORMATION TRANSMISSION SYSTEM

FIELD OF THE INVENTION

The present invention is related to a portable object and an information transmission system.

BACKGROUND OF THE INVENTION

Beverage containers that incorporate a tag for radio-frequency identification, abbreviated RFID, usually require the use of tags with loop antennas which are read by complex reader antennas.

Documents US 2012/0019417 A1, US 2011/0114647 A1 and U.S. Pat. No. 7,845,375 B2 show examples of beverage containers with tags.

SUMMARY OF THE INVENTION

In an embodiment, a portable object and an information transmission system may have a reduced size.

In an embodiment, a portable object comprises an integrated circuit, a first pad that is mechanically and electrically connected to the integrated circuit and a second pad that is mechanically and electrically connected to the integrated circuit. The portable object is designed for data transfer by capacitive coupling of the first pad to a first conducting line and of the second pad to a second conducting line, when the portable object is brought in vicinity to the first and the second conducting line.

It is an advantage that the two pads of the portable object are sufficient for data transfer and energy transfer. Thus, the size and the cost of an electronic component of the portable object can be reduced to a high extent.

In an embodiment, the portable object has such a small weight and small size that a user can carry it.

In an embodiment, the first and the second pad are arranged to the first and the second conducting line in a first phase of operation such that the first pad is capacitively coupled to the first conducting line and the second pad is capacitively coupled to the second conducting line for data transmission and the first and the second pad are detached from the first and the second conducting line in a second phase of operation that follows the first phase of operation.

In an embodiment, the coupling of the first and the second pad to the first and the second conducting line is configured such that an AC current flows between the pads and the conducting lines and a DC current between the pads and the conducting lines is prevented.

In an embodiment, the portable object comprises a strap that comprises the integrated circuit as well as the first and the second pad. The strap may be implemented as a RFID strap.

In an embodiment, an area of the first pad has a larger size than an area of the integrated circuit. An area of the second pad has a larger size than the area of the integrated circuit.

The first and the second pad may be essentially two-dimensional.

The first and the second pad may be basically rectangular.

In an embodiment, the first and the second pad are arranged on opposite edges of the integrated circuit.

In an embodiment, the portable object comprises a carrier which is attached on the first and the second pad. The carrier is realized as an insulating layer. The carrier is arranged between the first pad and the first conducting line and between the second pad and the second conducting line. The carrier electrically isolates the pads from the conducting lines.

In an embodiment, the integrated circuit comprises a supply circuit that is coupled to the first and the second pad, a modulator circuit that is coupled to the first and the second pad and a logic circuit that is coupled to a supply output of the supply circuit for power supply and to a control input of the modulator circuit. The integrated circuit may comprise an analog integrated circuit.

The integrated circuit can be realized as a RFID chip.

In an embodiment, the portable object is realized as an item of a group consisting of a container, a capsule, a cup and a card. The container may be configured to contain beverage or food. The capsule may be designed for containing beverage or food. The capsule can be implemented as a coffee capsule, a coffee pod or a coffee pad. The coffee capsule can for example be realized such that coffee beans or powder are packed in a plastic or aluminum package. The coffee pod, also called coffee pad, can for example be pre-packaged coffee beans or coffee powder in its own filter, especially paper filter. In certain non-English speaking countries, such as Germany and the Netherlands, the word "pad" is used instead of "pod".

The card can be a part from a group consisting of a chip card, a Subscriber Identify Module card, a System-Identification Module card, a memory card, a smart card, a signature card, a cash card and a credit card.

In an embodiment, the portable object is realized as a cartridge. The cartridge can be a drug cartridge.

The portable object can be a fast moving consumer good, abbreviated FMCG. The FMCG may be a product that is sold quickly and at relatively low cost. Examples include non-durable goods such as soft drinks, toiletries and grocery items.

The portable object may be a small object containing an electrically conducting material such as a metal or a liquid. Alternatively, the portable object may be a small object free of an electrically conducting material.

In an embodiment, an information transmission system comprises a portable object and a signal transfer arrangement. The portable object comprises an integrated circuit, a first pad that is mechanically and electrically connected to the integrated circuit and a second pad that is mechanically and electrically connected to the integrated circuit. The signal transfer arrangement comprises a first and a second conducting line such that selectively either the first pad capacitively couples to the first conducting line and the second pad capacitively couples to the second conducting line, when the portable object is in vicinity of the signal transfer arrangement, or the first and the second pad are decoupled from the first and the second conducting line, when the portable object is at a distance from the signal transfer arrangement.

It is an advantage of the information transmission system that the first capacitor between the first pad and the first conducting line and the second capacitor between the second pad and the second conducting line are sufficient to provide energy from the signal transfer arrangement to the portable object and to transfer data from the portable object to the signal transfer arrangement. By means of the capacitive coupling, a small size of the portable object is sufficient.

In an embodiment, the portable object is in vicinity of the signal transfer arrangement in the first state of operation. The portable object is at a distance from the signal transfer arrangement in the second state of operation.

In an embodiment, the coupling of the first and the second pad to the first and the second conducting line is free of an adhesive.

The first and the second conducting line can be parallel to each other.

The first and the second conducting line can be essentially two-dimensional.

In an embodiment, an extension of the first and the second pad is coordinated with an extension of the first and the second conducting line. For example, the first and the second pad and the first and the second conducting line have lateral extensions according to the equation:

$$A=A1+A2+A3 \geq D,$$

wherein A1 is an extension of the first pad, A2 is an extension of the integrated circuit, A3 is an extension of the second pad and D is the distance between the first conducting line and the second conducting line.

In an embodiment, the first and the second conducting line have a main direction. The signal transfer arrangement is designed such that the capacitive coupling of the first and the second pad to the first and the second conducting line is continued during a movement of the portable object in the main direction of the first and the second conducting line.

In an embodiment, the first and the second conducting line are arranged on a non-flat surface of the signal transfer arrangement.

The first and the second conducting line may have the form of circular arcs.

In an embodiment, the information transmission system comprises a reader or host that is electrically connected to the first and the second conducting line. The reader respectively host is designed to transmit energy to the portable object and to receive data from the integrated circuit of the portable object. Optionally, the reader respectively host is designed to send data to the integrated circuit of the portable object.

In an embodiment, the reader is a single-chip reader. The reader may comply with the HF and UHF Gen 2 RFID standards. UHF is the abbreviation for ultra high frequency. The reader may alternatively be operating between 15 and 150 kHz. The method can be used at any frequency range. The reader may be designed as a RFID reader.

In an embodiment, the signal transfer arrangement comprises an insulating layer attached to the first conducting line and at least one further pad electrically connected to the first conducting line by a via through the insulating layer. Moreover, the signal transfer arrangement may comprise a conductive layer. At least an additional pad may be electrically connected to the conductive layer or the second conducting line by a further via.

In an embodiment, the first and the second conducting line form a transmission line.

In an embodiment, the signal transfer arrangement comprises a third conducting line. The first, the second and the third conducting line form a coplanar waveguide.

In an embodiment, the portable object is free from a loop antenna which is coupled to the first and the second pad. Moreover, the reader or host is free from a loop antenna which is designed for communication with the portable object.

In an embodiment, the information transmission system is foreseen for wireless data transmission.

In an embodiment, a method for communication comprises arranging a portable object and a signal transfer arrangement to each other in a first phase of operation such that a first pad of the portable object is capacitively coupled to a first conducting line of the signal transfer arrangement and a second pad of the portable object is capacitively coupled to a second conducting line of the signal transfer arrangement. The first and the second pad are electrically connected to an integrated circuit of the portable object and data are transferred between the integrated circuit and the two conducting lines. Moreover, the portable object is detached from the signal transfer arrangement in a second phase of operation that follows the first phase of operation.

In an embodiment, the method and the information transmission system are configured for tagging, by using UHF RFID tag, of FMCGs, and are designed for reading UHF RFID antenna less tags of FMCGs. A complex reader antenna is not required. Also a special RFID transponder or tag antenna is not required. The RFID reader is able to communicate with the RFID transponder integrated circuit without use of antennas of the reader and of the tag. A communication between the reader and the tag is enabled by using an unbalanced transmission line connected to the RFID reader and the RFID transponder integrated circuit mounted on the strap having pads larger than a conventional RFID strap (for example 20-30% bigger pad area).

In an embodiment, the information transmission system, the portable object and the method for communication allow to reduce costs in implementation of a RFID enabled solution in FMCGs, especially soft drink, coffee, and in general any hot and cold drink system based on a RFID authentication and/or identification of cups or capsules ID and type prior to dispense the selected drink. A space occupied by the antenna is not required anymore and tag size can for example be reduced 60% or more in comparison to conventional tags. Tag costs are highly reduced by means of size reduction of the RFID tag.

BRIEF DESCRIPTION OF THE DRAWINGS

The following description of figures of exemplary embodiments may further illustrate and explain the application. In so far as components, elements or devices correspond to one another in terms of their function in different figures, the description thereof is not repeated for each of the following figures.

FIGS. 2A, 2B, 3 to 7, 8A to 8C, 9A to 9D, 10A to 10C, 11 and 12 show exemplary embodiments of an information transmission system.

FIGS. 19A, 19B, 20A and 20B show further exemplary embodiments of an information transmission system.

DETAILED DESCRIPTION OF THE DRAWINGS

Figure 1A:
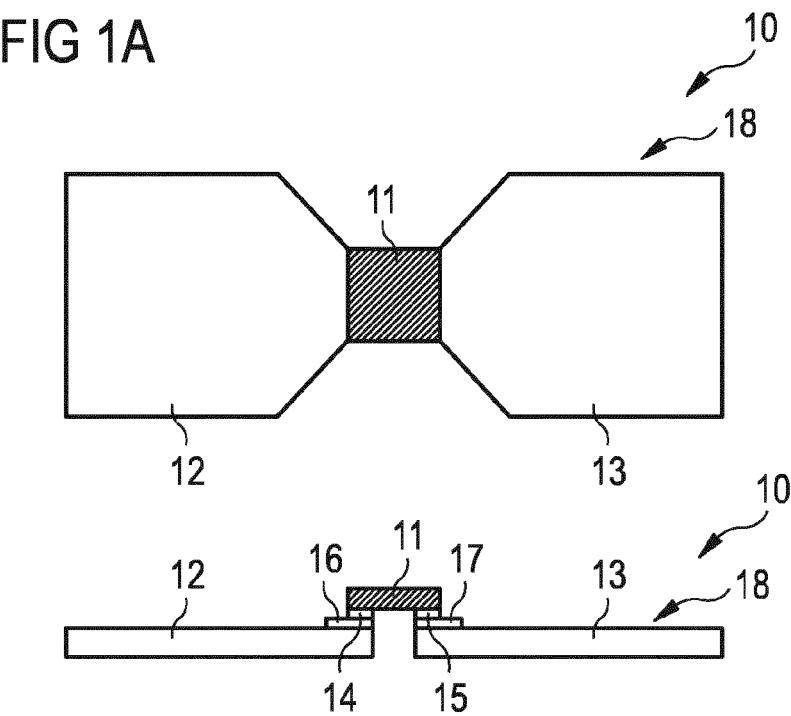
FIGS. 1A and 1B show exemplary embodiments of a portable object.

FIG. 1A shows an exemplary embodiment of a portable object 10 in a cross-section and in a top view. The portable object 10 comprises an integrated circuit 11 and a first and a second pad 12, 13. The integrated circuit 11 is directly electrically connected to the first and the second pad 12, 13. The integrated circuit 11 comprises a first and a second RF pad 14, 15. Moreover, the portable object 10 comprises a first and a second conductive glue spot 16, 17. The integrated circuit 11 is mechanically and electrically connected to the first pad 12 via the first RF pad 14 and the first conductive glue spot 16 and additionally to the second pad 13 via the second RF pad 15 and the second conductive glue spot 17. The coupling of the integrated circuit 11 to the first and the second pad 12, 13 is configured such that a DC electrical current can flow from the integrated circuit 11 to the first and the second pad 12, 13.

The first and the second pad 12, 13 are arranged on opposite edges of the integrated circuit 11. In the top view, the area of the first pad 12 has a larger size in comparison to the area of the integrated circuit 11. Moreover, the area of the second pad 13 has a larger size in comparison to the area of the integrated circuit 11. The first and the second pad 12, 13 have approximately the same size. The areas of the first and the second pad 12, 13 basically have a rectangular form. The first and the second pad 12, 13 contain a metal, such as aluminum or copper. A strap 18 comprises the integrated circuit 11 and the first and the second pad 12, 13.

Figure 1B:
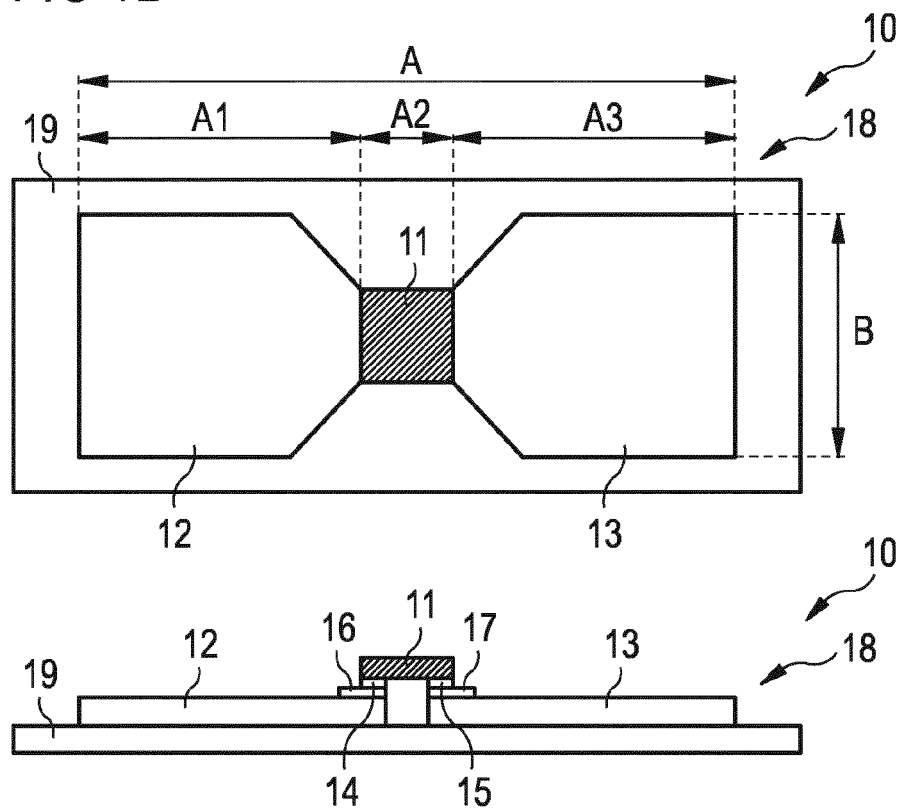

FIG. 1B shows a further exemplary embodiment of the portable object 10 which is a further development of the portable object shown in FIG. 1A. The integrated circuit 11 and the first and the second pad 12, 13 are attached to a carrier 19 of the portable object 10. The carrier 19 is realized as an isolating carrier. The carrier 19 is non-conductive. The carrier 19 is made of dielectric insulating material. The carrier 19 contains a material such as PTFE or PET. The first and the second pad 12, 13 are directly arranged on the carrier 19. The carrier 19 has a rectangular form. The carrier 19 is realized as a sheet. The carrier 19 may be fabricated from a flexible foil. The carrier 19 is flexible. The strap 18 comprises the carrier 19. The carrier 19 acts as a basis for the first and the second pad 12, 13 and the integrated circuit 11.

The first and the second pad 12, 13 and the integrated circuit 11 have a first extension A and a second extension B. The second extension B is smaller than the first extension A. The second extension B is the width of the first pad 12 and the second pad 13. The first extension A is the sum of an extension A1 of the first pad 12, an extension A2 of the integrated circuit 11 and an extension A3 of the second pad 13.

The strap 18 is realized as a RFID strap or RFID tag. The integrated circuit 11 is fabricated as a die or chip. The integrated circuit 11 is implemented as a microchip. The size of the integrated circuit 11 may be less than 1 mm square. The pads 12, 13 are conductive parts and are fabricated from a metallization layer. The pads 12, 13 can be named conductive contact parts. The pads 12, 13 are etched, printed or attached on the carrier 19. The integrated circuit 11 is attached to the pads 12, 13 by using electrically conductive glue spots 16, 17. The integrated circuit 11 is flip-chip mounted on the carrier 19. The strap 18 can be fabricated by high-speed roll-to-roll manufacturing. Typical dimensions of the strap 18 are for example 10 mm×2.5 mm with side pads 12, 13 of 2.5 mm×3 mm.

The strap 18 is used to ease the assembling. The integrated circuit 11 may also be named as RFID integrated circuit. By means of oversized pads 12, 13 the attachment of the RFID integrated circuit 11 to another body is simplified. Contrary to that, in conventional flip-chip manufacturing the microchip is a very small component with tiny contact pads that have to be very precisely placed on an antenna. This can be a relatively slow process.

In an alternative, not shown embodiment, the portable object 10 comprises at least a further pad which is connected to the integrated circuit 11.

Figure 2A:
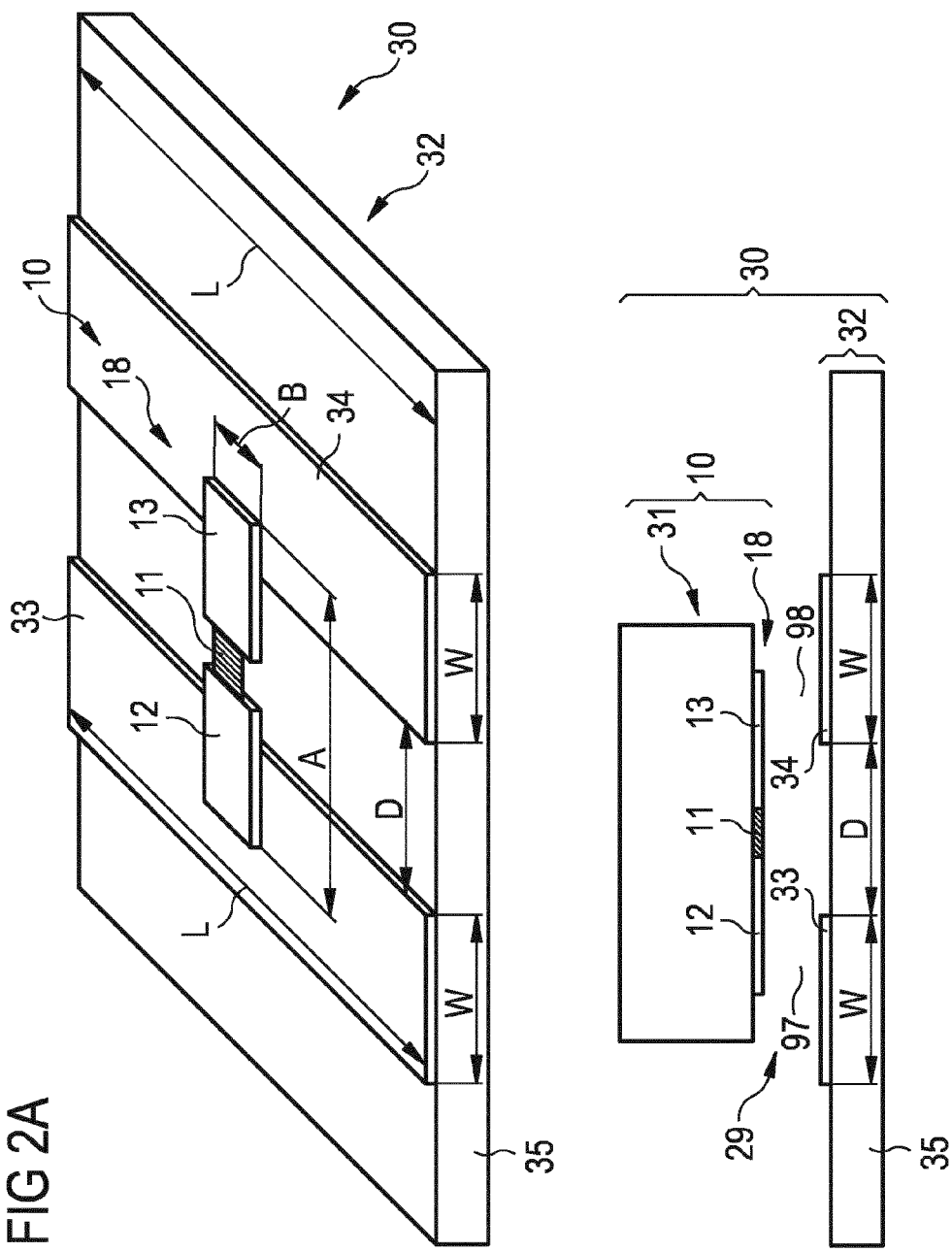

FIG. 2A shows an exemplary embodiment of an information transmission system 30 in a cross-section and in a side view. The portable object 10 additionally comprises an item 31 on which the strap 18 is arranged. Thus, the integrated circuit 11, the first and the second pad 12, 13 are arranged on the item 31. The information transmission system 30 comprises the portable object 10 and a signal transfer arrangement 32. The signal transfer arrangement 32 is designed for signal and energy transfer to the portable object 10. The signal transfer arrangement 32 comprises a first and a second conducting line 33, 34. The first and the second conducting line 33, 34 form a transmission line. The first and the second conducting line 33, 34 are straight or linear lines. The first and the second conducting line 33, 34 have a main direction. The signal transfer arrangement 32 comprises a carrier body 35 on which the first and the second conducting line 33, 34 are attached. The carrier body 35 is a flexible body or a rigid body. The carrier body 35 is non-conductive. The carrier body 35 can be a printed circuit board, abbreviated PCB, or a flexible circuit. The first and the second conducting line 33, 34 are parallel. As also illustrated in FIG. 1B, the first and the second pad 12, 13 and the integrated circuit 11 have the first extension A. The first and the second conducting line 33, 34 have a distance D. The two conducting lines 33, 34 are separated by the distance D. Moreover, the first conducting line 33 has a width W and a length L. The second conducting line 34 has approximately the same width W and the same length L. The extensions follow the equations:

$$A = A1 + A2 + A3 \geq D$$

and $$D + 2 \cdot W \geq A$$

As shown in the cross-section, the first pad 12 is capacitively coupled to the first conducting line 33 via an air gap 29. Also, the second pad 13 is capacitively coupled via the air gap 29 to the second conducting line 34. The first pad 12 and the first conducting line 33 overlap such that a first parallel capacitor 97 is formed by the first pad 12 and the first conducting line 33. The overlap of the second pad 13 and of the second conducting line 34 results in a second parallel capacitor 98 formed by the second pad 13 and the second conducting line 34. Due to the length L of the first and the second conducting line 33, 34 the portable object 10 can be placed on a plurality of sites on the first and the second conducting line 33, 34. The length L is larger than the second extension B of the first pad 12. The length L is larger than the width W of the first conducting line 33. The portable object 10 can also move in the main direction of the first and the second conducting line 33, 34 without losing the electrical coupling between the first and the second pad 12, 13 and the first and the second conducting line 33, 34.

FIG. 2B is a further exemplary embodiment of the information transmission system 30 which is a further development of the embodiments shown in FIGS. 1A, 1B and 2A. The first and the second conducting line 33, 34 are arranged at a first surface of the carrier body 35. The first surface of the carrier body 35 is flat. An insulating layer 37 is fabricated on the first and the second conducting line 33, 34. The insulating layer 37 covers the first and the second conducting line 33, 34 and the first surface of the carrier body 35. As shown on the left side of the lower part of FIG. 2B, the portable object 10 is arranged on the first surface of the carrier body 35. The portable object 10 comprises the carrier 19, wherein the carrier 19 is arranged between the first and the second conducting line 33, 34 and the first and the second pad 12, 13. The first pad 12 is isolated by the carrier 19, the air gap 29 and the isolating layer 37 from the first conducting line 33. Correspondingly, the second pad 12 is isolated by the carrier 17, the air gap 29 and the isolating layer 37 from the second conducting line 34.

As shown in the upper part and on the right side of the lower part of FIG. 2B, the portable object 10' can alternatively be arranged at a second surface of the carrier body 35 that is opposite to the first surface of the carrier body 35. The upper part illustrates the two sites where the portable object 10, 10' can be placed. In general, only one of the two objects, either the portable object 10 or the portable object 10', is attached at the signal transfer arrangement 32.

The first and the second conducting line 33, 34 are implemented as two parallel traces that form a transmission line. The first and the second conducting line 33, 34 are parallel to each other such as two rails of a railway. The strap 18 is coupled to the transmission line. Thus, the strap 18 is used without any connection to an antenna. The strap 18 is capacitively coupled to the transmission line, thus no electrical connection is needed. The strap 18 can be named a tag or a RFID tag. The communication between a not shown RFID reader 80 and the strap 18 occurs through signal propagation along the transmission line and capacitive coupling to the strap 18. The transmission line and the strap 18 are isolated by dielectric materials (solder mask/solder block or the substrate 35 itself of the transmission line, plus the PTFE or PET coating 19 of the strap 18). The strap 18 can be placed either direct on top of the transmission line or on the back side of the carrier body 35. Between the transmission line and the pads 12, 13 only dielectric layers are present. The transmission line can be implemented on rigid PCB or on a flexible circuit.

FIG. 3 shows a further exemplary embodiment of the information transmission system 30. A conducting layer 38 is fabricated on the second surface of the carrier body 35. The conducting layer 38 contains a metal. The portable object 10 is located at the first surface of the carrier body 35. The carrier body 35 is realized as a PCB. The conducting layer 38 forms a ground plane. Thus, the transmission line is formed by two parallel traces realized by the first and the second conducting line 33, 34 and the ground plane implemented by the conducting layer 38. The strap 18 is coupled to the transmission line. In case of transmission line with ground plane insulation, due to physic/theory of electric field propagation, the strap 18 cannot be placed on the second surface of the carrier body 35 that means the bottom side of the PCB and can only be placed on top of it, in order to be able to couple in an efficient way with the transmission line.

FIG. 4 shows a further exemplary embodiment of the information transmission system 30 which is a further development of the above-shown embodiments. A third conducting line 39 is arranged on the carrier body 35. The first conducting line 33 is between the third conducting line 39 and the second conducting line 34. The third conducting line 39 has a distance D' to the first conducting line 33. The distance D' between the first and the third conducting line 33, 39 is equal to the distance D between the first and the second conducting line 33, 34.

The first, the second and the third conducting line 33, 34, 39 also form a transmission line. The signal transfer arrangement 32 comprises the third conducting line 39. The first, the second and the third conducting line 33, 34, 39 are implemented as a coplanar waveguide, abbreviated CPW. The signal transfer arrangement 32 comprises the CPW. The conducting line which is in the middle between the other two conducting lines is a signal line. The outer conducting lines are ground reference lines. According to FIG. 4, the first conducting line 33 is the signal line and the second and the third conducting line 34, 39 are the ground reference lines. Thus, the first conducting line 33 is in the middle between the second and the third conducting line 34, 39. As shown in FIG. 4, the portable object 10 can be attached to the first surface or, alternatively, to the second surface of the carrier body 35.

The strap 18 is coupled to the CPW. In the CPW, the center trace is the signal line and the side traces are the ground reference line. Due to field distribution in the CPW, in order to achieve efficient coupling between the strap 18 and the transmission line, the strap 18 has to be placed between the signal line and one of the ground reference lines. The strap 18 can be located direct on top of the traces or on bottom side of the PCB respectively flexible circuit 35.

Figure 5:
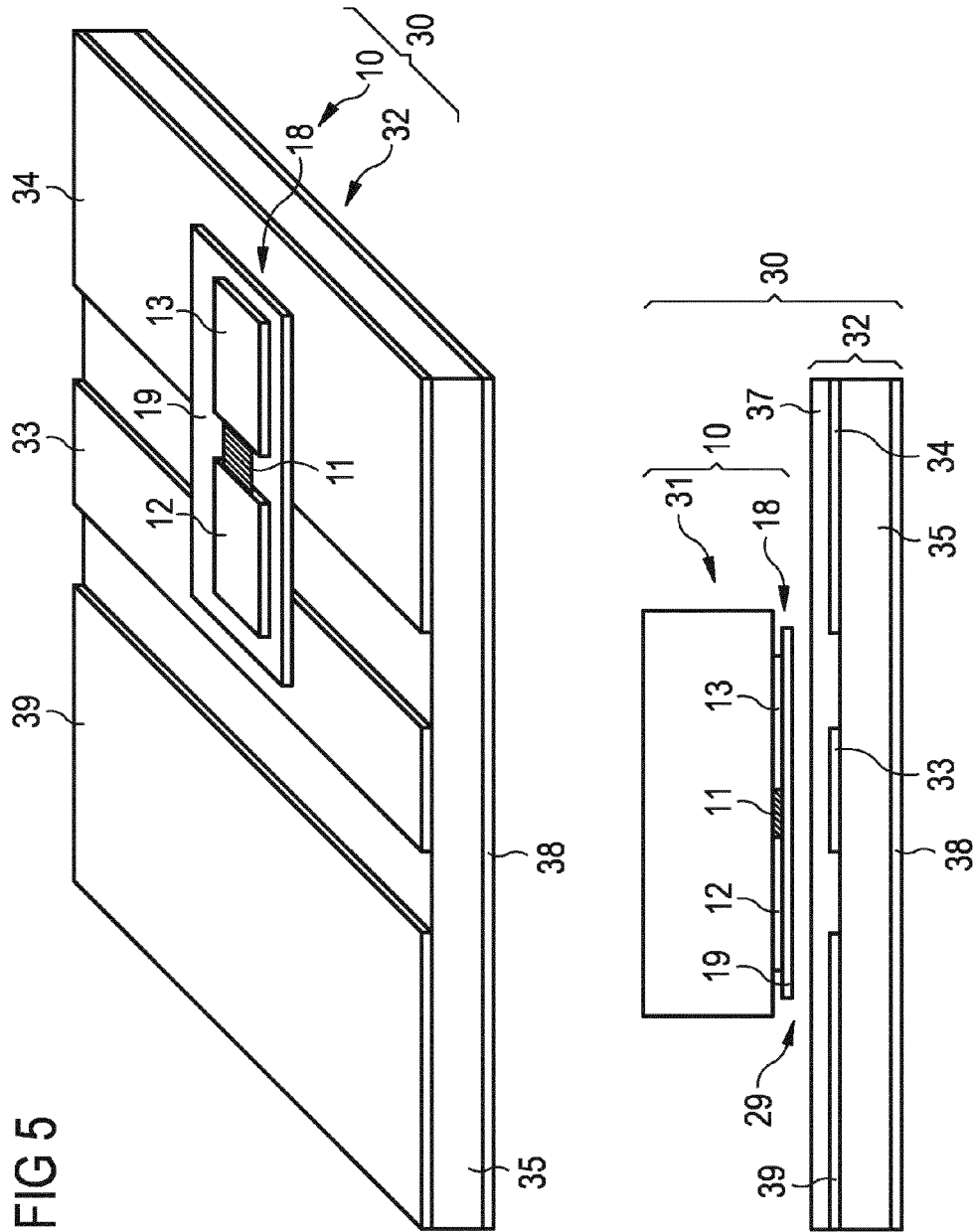

FIG. 5 shows a further exemplary embodiment of the information transmission system 30 which is a further development of the above-shown embodiments. The conducting layer 38 is fixed on the second surface of the carrier body 35. The third conducting line 39 is fabricated on the first surface of the carrier 35. Thus, the portable object 10 can only be attached to the first surface of the carrier body 35. The portable object 10 can be arranged such that the first and the second pad 12, 13 are capacitively coupled to the first and the second conducting line 33, 34, but the portable object 10 can alternatively also be arranged such that the first and the second pad 12, 13 are capacitively coupled to the first and the third conducting line 33, 39. The coplanar waveguide is realized as a grounded CPW, abbreviated GCPW. In case of grounded CPW due to presence of the ground layer 38 under the carrier body 35, the strap 18 can be placed only on top of the carrier body 35.

FIG. 6 shows a further exemplary embodiment of the information transmission system 30 which is a further development of the above-shown embodiments. The first and the second conducting line 33, 34 are curved. The first and the second conducting line 33, 34 may have the form of a half-circle, a circle arc or a circle. The first surface of the carrier body 35 can have a three-dimensional form. The carrier body 35 can have the form of a cylinder, cone, hemisphere or another non-flat three-dimensional form. The first and the second conducting line 33, 34 are located on the inner wall of the cylinder, cone, hemisphere or other non-flat three-dimensional form. The two parallel traces 33, 34 forming the transmission line are fixed on a circular substrate 35 with or without ground 38. The transmission line configuration having the two traces 33, 34 do not follow a straight line direction, but follow a curved path on a plane of the carrier body 35.

FIG. 7 shows a further exemplary embodiment of the information transmission system 30 which is a further development of the above-shown embodiments. The third conducting line 39 is arranged on the first surface of the carrier body 35. Thus, a coplanar waveguide is attached to the three-dimensional and non-flat carrier body 35. The CPW is realized on a circular substrate 35 with or without ground 38 and the strap 18 is coupled to it. The CPW is implemented as a curved CPW. As for the previous example, in case of CPW, the strap 18 has to be placed between the signal and the ground line to ensure correct coupling.

Figure 8A:
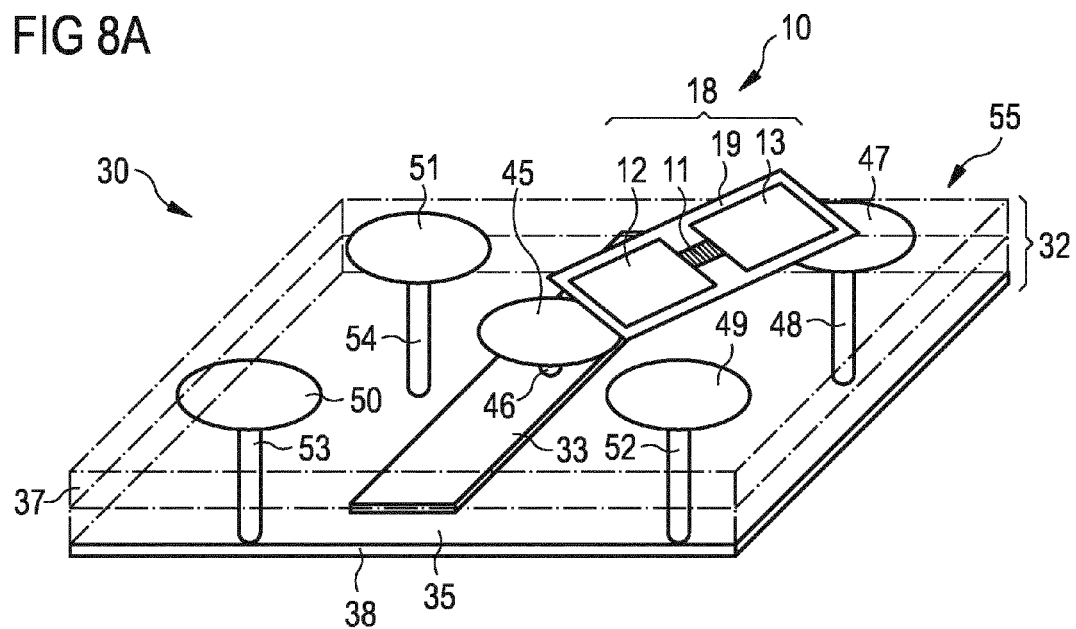

FIG. 8A shows a further exemplary embodiment of the information transmission system 30 which is a further development of the above-shown embodiments. The signal transfer arrangement 32 comprises the first conducting line 33, the carrier body 35 and the insulating layer 37. Moreover, the signal transfer arrangement 32 comprises a further pad 45 which is on the top surface of the insulating layer 37 and is connected to the first conducting line 33 by a via 46. The signal transfer arrangement 32 also comprises an additional pad 47 that is on the top surface of the insulating layer 37 and is connected by a further via 48 to the conducting layer 38. The further pad 45 and the additional pad 47 have such a distance that the first and the second pad 12, 13 can couple to the further and the additional pad 45, 47. The second conducting line 34 can be implemented by the conducting layer 38. The conducting layer 38 in FIGS. 8A to 8C has the same function as the second conducting line 34 in FIGS. 2 to 7.

The portable object 10 is arranged on the signal transfer arrangement 32 such that the portable object 10 can communicate to the first conducting line 33 and the conducting layer 38 by means of the further and the additional pad 45, 47. The signal transfer arrangement 32 comprises three more additional pads 49 to 51 which are electrically connected to the conducting layer 38 by further vias 52 to 54. The additional pads 47, 49, 50, 51 are arranged such that they are located at the corners of a rectangular area on the first surface of the signal transfer arrangement 32, wherein the further pad 45 is in the middle of the rectangular area.

The isolating layer 37, the first conducting line 33, the carrier body 35 and the conducting layer 38 can be realized as parts of a PCB. The PCB can be implemented as a multi-layer PCB. The carrier body 35 and the isolating layer 39 can be formed by isolating layers of the multi-layer PCB. The first conducting line 33 and the conducting layer 38 can be fabricated as metallization layers of the multi-layer PCB. The distance of the further pad 45 to the additional pads 47, 49, 50, 51 is approximately equal. Thus, the portable object 10 can be attached to four different sites on the first surface of the signal transfer arrangement 32 for communication.

The first conducting line 33 and the conducting layer 38 form a strip-line. The strip-line in a multilayer structure including the pads 45, 47, 49, 50, 51 connected to signal and ground plane creates an ad-hoc electric field distribution in order to allow coupling between the strip-line and the strap 18. Coupling between the strap 18 and signal propagating through the transmission line is implemented by the pads 45, 47, 49, 50, 51 that are placed in a different layer with respect to the signal line 33 and the ground 38. The pads 45, 47, 49, 50, 51 are connected to the signal line 33 and to the reference ground 38. By doing this an electric field is created between the further pad 45 connected to the signal line 33 and the additional pads 47, 49, 50, 51 connected to the ground layer 38 (they act as capacitors, in the example shown in FIG. 8A as four different capacitors). When the strap 18 is placed in between the further pad 45 connected to the signal line 33 and one of the additional pads 47, 49, 50, 51 connected to the ground layer 38, it capacitively couples to both pads and allow signal and energy transmission from the signal line 33 to the integrated circuit 11 and consequently communication between the RFID reader 80 and the integrated circuit 11.

Figure 8B:
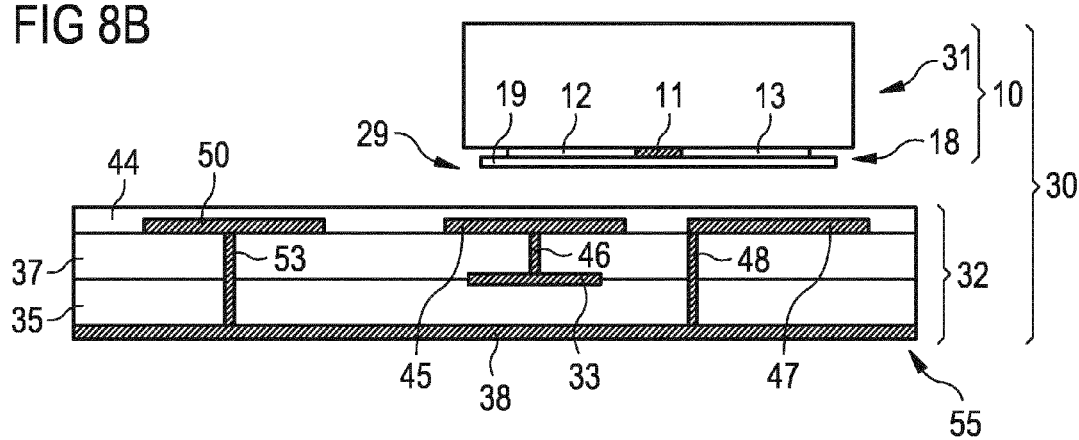

FIG. 8B shows a cross-section of the information transmission system 30 shown in FIG. 8A. The pads 45, 47, 49, 50, 51 can have a circular shape, a rectangular shape, a quadratic shape or any other shape. The via 53 is located such that it connects the middle of the additional pad 50 the conductive layer 38. Alternatively, the via can connect another point of the pad, for example it can connect an edge of the pad to the conducting layer 38, as shown by the additional pad 49 and the via 52 on the right-hand side of the cross-section shown in FIG. 8B.

The signal transfer arrangement 32 comprises pads 45, 47, 49, 50, 51 that are used to couple with the strap 18 and placed in a different layer. The center pad 45 is electrically connected to the signal line 33 and the surrounding pads 47, 49, 50, 51 are connected to the signal reference ground 38. The strap 18 is not directly electrically connected to the pads 45, 47, 49, 50, 51 but separated by a further insulating layer 44. This configuration is advantageous, when a high integration is needed. The signal transfer arrangement 32 can comprise at least a further layer under the reference ground layer 38, where at least an electronic device is placed. The electronic device can be a RFID Reader integrated circuit or an interface to a network or to a personal computer.

In an alternative, not shown embodiment, the additional pads 47, 49 to 51 are electrically connected to the second conducting line 34 by the further vias 48, 52 to 54.

FIG. 8C shows a further exemplary embodiment of the information transmission system 30 which is a further development of the embodiment shown in FIGS. 8A and 8B. The information transmission system 30 comprises more than one of the unit 55 of the signal transfer arrangement 32 shown in FIG. 8A. The unit 55 shown in FIG. 8A comprises the further pad 45 that is connected to the first conducting line 33 and at least one additional pad 47, 49, 50, 51. The signal transfer arrangement 32 of FIG. 8C comprises a plurality of units 55, each having a pad connected to a conducting line and at least one additional pad connected to the conducting layer 38. As shown in FIG. 8C, the conducting lines of the different units 55 to 60 are connected to the same conducting line which is the first conducting line 33. Thus, the strap 18 can be placed on the first surface of the signal transfer arrangement 32 on several sites for communication. The signal transfer arrangement 32 can be interconnected with another signal transfer arrangement for enhancing the reading area.

In an alternative, not-shown embodiment, the conducting lines of the different units 55-60 are not connected to each other. Thus, a strap 18 located on the signal transfer arrangement 32 may selectively communicate to different conducting lines. The portable object 10 may comprise more than one strap 18. The portable object 10 may be arranged on top of the first surface of the signal transfer arrangement 32 such that the plurality of straps 18 communicates to the plurality of units 55 to 60 of the signal transfer arrangement 32.

Figure 9C:
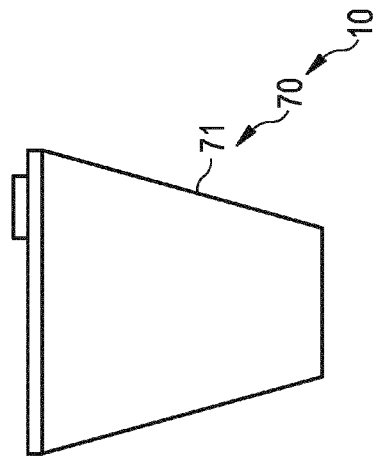
Figure 9D:
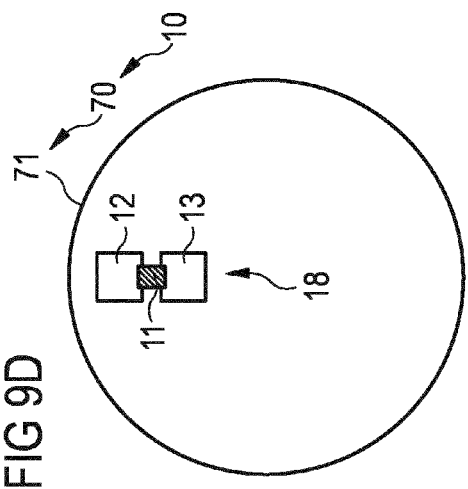
Figure 9B:
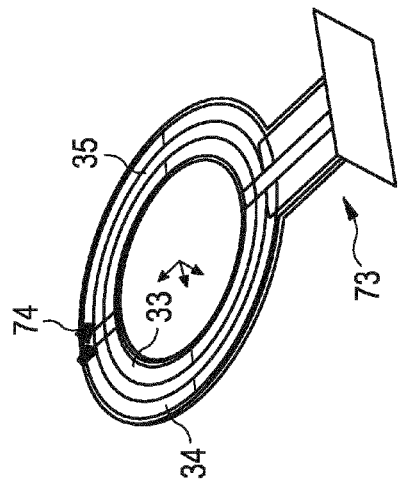
Figure 9A:
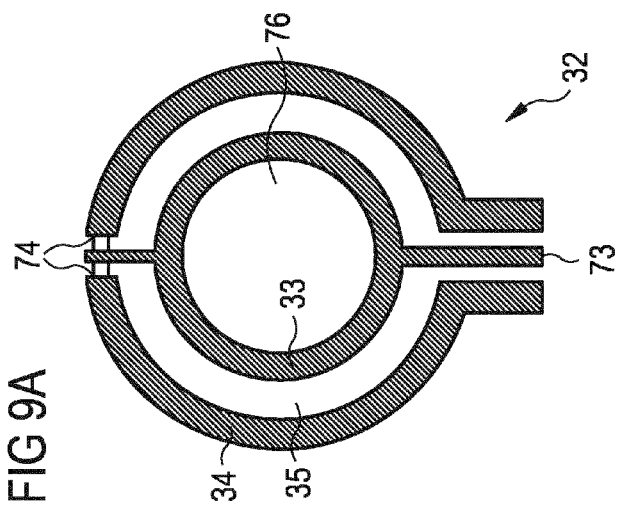

FIGS. 9A to 9D show a further exemplary embodiment of the information transmission system 30 which is a further development of the above-shown embodiments. The portable object 10 is realized as a container 70. The container 70 can be implemented as a capsule 71. The capsule 71 contains a liquid. The capsule 71 is realized as a coffee capsule or coffee pod or coffee pad. The strap 18 is arranged at the outside of the container 70. The strap 18 is arranged near the top of the container 70. Furthermore, the information transmission system 30 comprises a fluid dispensing system 72, not shown, which comprises the signal transfer arrangement 32. The fluid dispensing system 72 is implemented as a coffee machine 72'. The signal transfer arrangement 32 is designed such that it has a hole 76 for inserting the container 70. The hole 76 can also be named an opening. The signal transfer arrangement 32 surrounds the hole 76. The first and the second conducting line 33, 34 are arranged in a circular form. The first and the second conducting line 33, 34 encircle the hole 76. Moreover, the signal transfer arrangement 32 comprises a feeding point 73 for providing contact to the first and the second conducting line 33, 34. The signal transfer arrangement 32 comprises a termination 74. The termination 74 provides that the transmission line realized by the first and the second conducting line 33, 34 obtains its characteristic impedance value. FIG. 9A shows the top view on the signal transfer arrangement 32, whereas FIG. 9B shows a three-dimensional view on the signal transfer arrangement 32. The side view of the container 70 is shown in FIG. 9C, whereas a top view of the container 70 is illustrated by FIG. 9D.

The transmission line configuration is able to read the strap 18 mounted on the capsule 71. The information transmission system 30 can be implemented in or by the coffee machine 72'. An initial CPW matched to a not-shown RF cable 79 and consequently to the reader 80 is split into two branches having characteristic impendence that keep the transmission line matched at the splitting point dividing the power received from reader 80 by two and distributing it to the two branches of the transmission line. The structure is circular like all the majority of capsules 71 and has the hole 76 in the middle needed to allow to the coffee machine 72' to operate correctly. A series of needles are normally placed in the middle of the capsule 71 to pump water into it and allow coffee brewing. The capsule 71 is equipped on top of it with the strap 18 in a way that the strap 18 will be aligned with the two traces 33, 34 during operation.

Figure 10C:
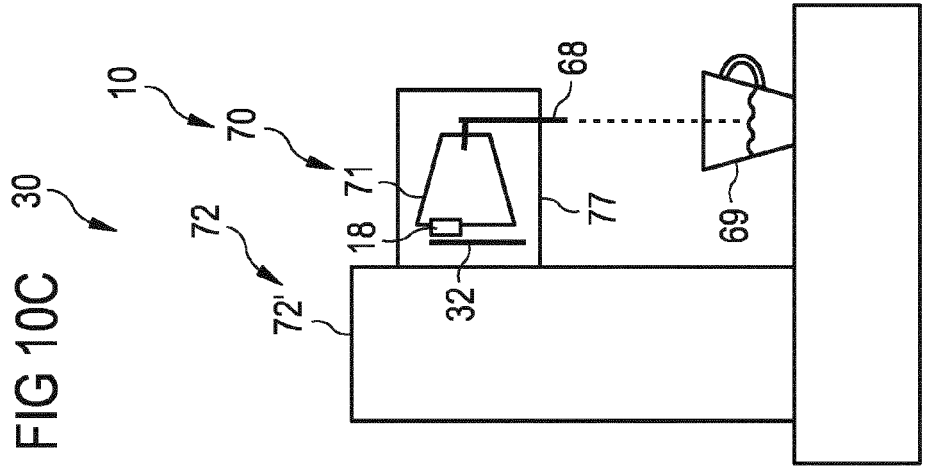
Figure 10B:
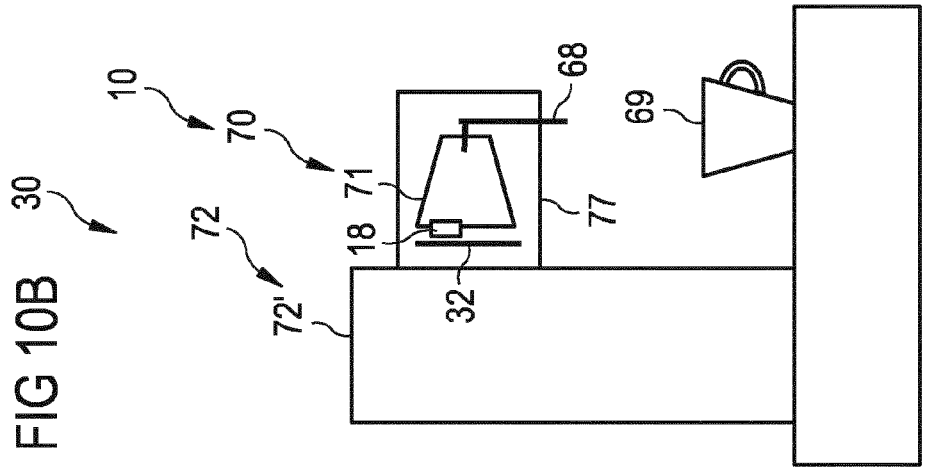
Figure 10A:
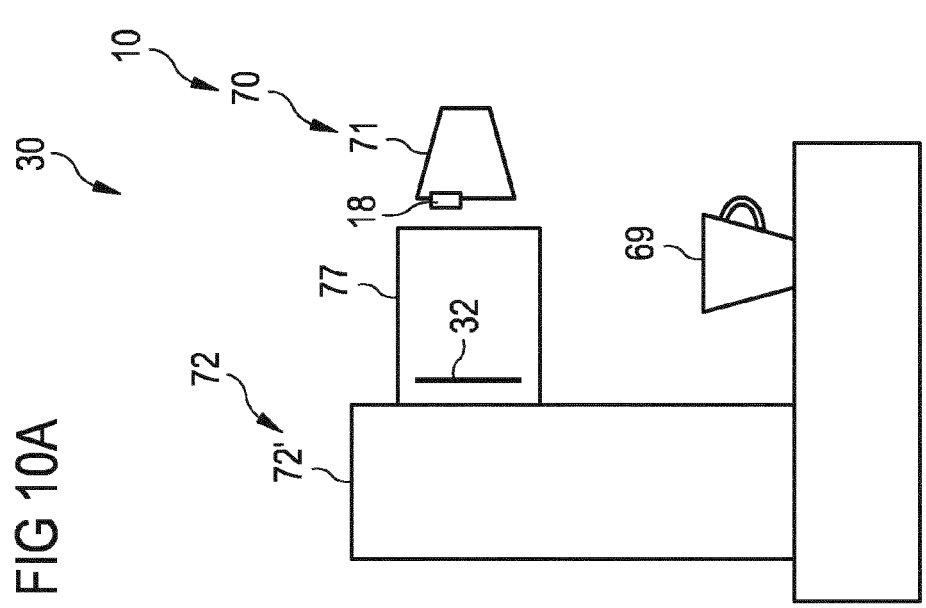

FIGS. 10A to 10C show a further exemplary embodiment of the information transmission system 30 which is a further development of the above-shown embodiments. FIG. 10 shows a schematic view of the fluid dispensing system 72, which is implemented as the coffee machine 72'. As shown in FIG. 10A, before a first phase of operation, the container 70 is not attached to the fluid dispensing system 72. During this phase of operation, the portable object 10 does not couple to the first and the second transmission line 33, 34. In the first phase of operation which is illustrated by FIGS. 10B and 10C, the portable object 10 is in close proximity to the fluid dispensing system 72. Thus, in the first phase of operation, the portable object 10 is arranged to the signal transfer arrangement 32 such that the first and the second pad 12, 13 are capacitively coupled to the first and the second conducting line 33, 34 for data transmission. During a first sub-phase of the first phase of operation phase shown in FIG. 10B, the coffee machine 72 communicates with the container 70, for example, the information transmission system 30 recognizes for which drink or which sort of coffee or coffee-based mixture the container 70 is foreseen. In a second sub-phase of the first phase of operation shown in FIG. 10C, the coffee machine 72 provides the coffee or coffee based mixture to a cup 69 through a tube 68.

In a second phase of operation, the container 70 is detached from the fluid dispensing system 72. The portable object 10 is removed from the signal transfer arrangement 32 and, therefore, the first and the second pad 12, 13 are detached from the first and the second conducting line 33, 34. In the second phase of operation, a user can take the cup 69 for drinking and the capsule 71 is removed from the coffee machine 72'. The second phase of operation can be illustrated by FIG. 10A. The difference is that the capsule 71 is empty and the cup 69 is filled in the second phase of operation.

The integrated circuit 11 comprises a memory 106 with a number. The fluid dispensing system 72 is configured to receive the number via the signal transfer arrangement 32 and to select one of several methods of operation of the fluid dispensing system 72 according to this number. In the different methods of operation, the fluid dispensing system 72 dispenses different drinks or brews different sorts of coffee or coffee-based mixtures.

In an alternative embodiment, the memory 106 of the integrated circuit 11 stores the information regarding which drink, which kind of coffee or coffee-based mixture is wanted by the user. The fluid dispensing system 72 receives this information via the signal transfer arrangement 32 and selects the appropriate method of operation for providing the specified drink or sort of coffee or coffee-based mixture.

The transmission line as shown in FIG. 9 is mounted on the coffee machine 72'. The transmission line described in the Figures above is connected to the RFID reader 80 via the RF cable 79 and is embedded into the coffee machine 72' exactly in the area, where the capsule 71 will be in contact with needles in order to allow brewing. The capsule 71 is placed into the holder 77 and by means of a mechanical system, manually or automatic, will be coupled with the needles and consequently the transmission line will be coupled with the strap 18 placed on top of the capsule 71. At this point of time the first phase of operation starts during which the reader 80 is able to identify the capsule 71 and read out information from the RFID integrated circuit tag. The information received from the RFID tag will be transferred to the central processing unit, abbreviated CPU, of the coffee machine 72' and the coffee machine 72' will enable (if the container 70 or the capsule 71 is the proper one) the brewing of the correct coffee based mixtures/drink or any other drink without any selection from the user. The user will need only to start the information transmission system 30 that incorporates the coffee machine 72' and said system 30 will select the proper brewing configuration automatically according with the identified container 70. When the container 70 is removed, the reader 80 will recognize that the container 70 is not present any more and will send the information regarding the non-presence to the CPU that will place the coffee machine 72' in standby mode. The CPU of the coffee machine 72' is a microcontroller.

Figure 11:
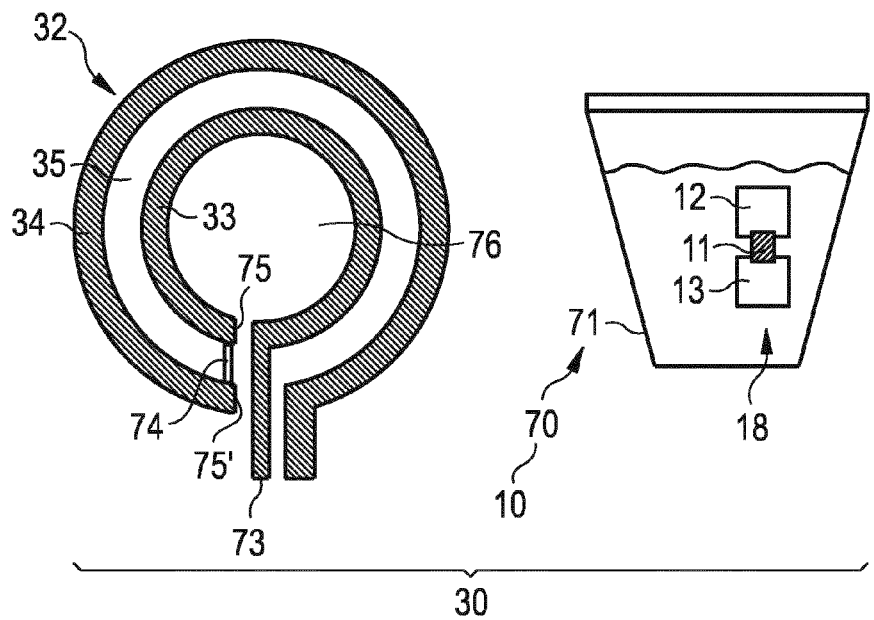

FIG. 11 shows an alternative embodiment of the information transmission system 30 which is a further development of the above-shown embodiments. The strap 18 is arranged in the lower half of the container 70. The first and the second conducting line 33, 34 have an approximately circular form. However, the first and the second conducting line 33, 34 do not comprise a complete circle. The end 75 of the first conducting line 33 is coupled to the end 75' of the second conducting line 34 via the termination 74. The parallel trace transmission line can be placed around the holder 77 of the container 70 and the strap 18 is placed on the side of the container 70. When the container 70 is placed into the machine holder 77, the strap 18 is aligned with the transmission line and couples with it. When a user puts the container 70 into the signal transfer arrangement 32, the strap 18 is aligned to the first and the second conducting line 33, 34.

Figure 12:
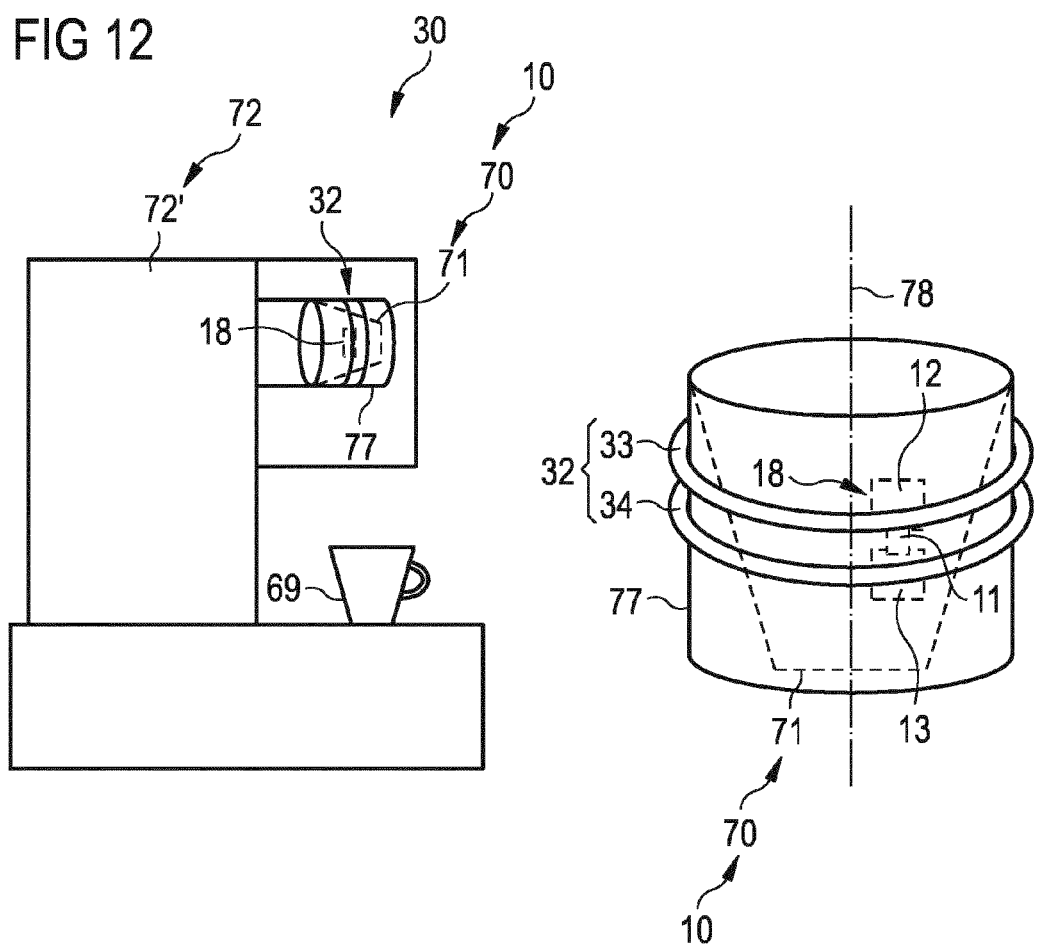

FIG. 12 shows an alternative embodiment of the information transmission system 30 which is a further development of the above-shown embodiments. As shown on the right side of FIG. 12, the container 70 is inserted into the holder 77. The signal transfer arrangement 32 is arranged on the outside of the holder 77. Thus, the first and the second conducting line 33, 34 are attached at the outside of the holder 77. The holder 77 has such a form that the strap 18 on the container 70 is brought into close vicinity to the first and the second conducting line 33, 34. The container 70 and the holder 77 are fabricated such that the two pads 12, 13 are capacitively coupled to the two conducting lines 33, 34. The first and the second conducting line 33, 34 have an approximately circular form. The container 70 has a rotational symmetry to a middle axis 78. Thus, the strap 18 does not have to be fixed on exactly one site to achieve a communication between the integrated circuit 11 and the coffee machine 72'. The coffee machine 72' is able to communicate with the container 70 at different angles of rotation of the container 70 related to the middle axis 78.

The parallel trace transmission line is designed to be able to read the strap 18 mounted on the side of the container 70. The parallel traces are placed on the coffee machine 72' in order to be able to read the strap 18 placed on the side of the container 70. The system works as described in FIG. 11. The transmission line is now placed inside the container holder 77 and the information transmission system 30 will be able to identify the container 70 immediately after it will be placed into the machine 72. This takes place, before the container 70 will be coupled with needles.

The portable object 10 may be realized as food or beverage container comprising the strap 18.

In an alternative, not shown embodiment, the portable object 10 is realized as the cup 69 comprising the strap 18. The cup 69 may be a coffee cup. The coffee machine 72' may comprise the signal transfer arrangement 32 at the place, where the cup 69 is applied by the user. The coffee machine 72' identifies the cup 69 in the first phase of operation and provides the desired drink such as soft-drink, tea, coffee or coffee-based mixture.

Figure 13:
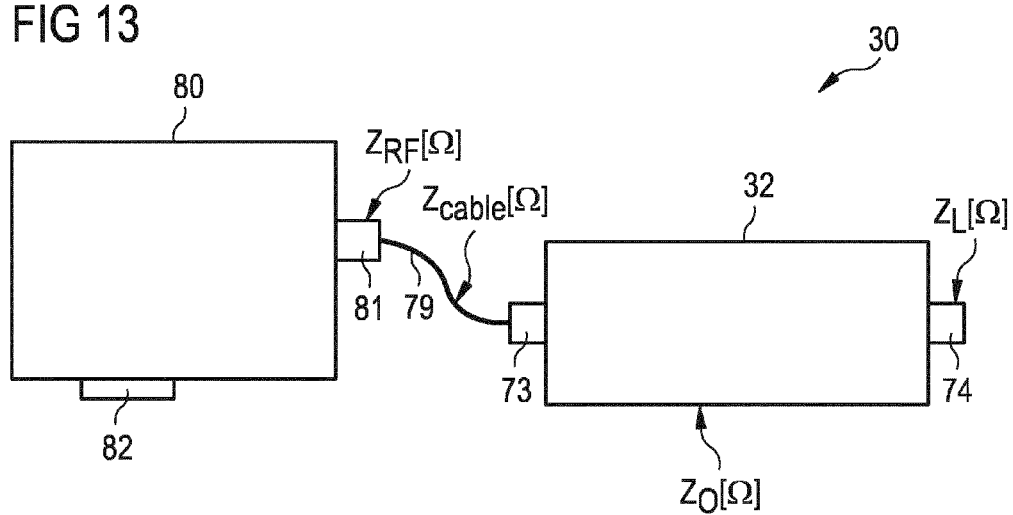
FIG. 13 shows an exemplary embodiment of an electronic system comprised by an information transmission system.

FIG. 13 shows an exemplary embodiment of an electronic system comprised by the information transmission system 30 shown above. The information transmission system 30 comprises the signal transfer arrangement 32, the cable 79 and the reader 80. The signal transfer arrangement 32 comprises the transmission line. The transmission line can be realized as a CPW, a grounded CPW, a strip line or another type of transmission line. The signal transfer arrangement 32 is configured to be coupled to the strap 18 of the portable object 10. The transmission line has a termination 74 on one end of the transmission line and is connected on its other side to the cable 79. The cable 79 is realized as an RF cable. The cable 79 couples the signal transfer arrangement 32 to the reader 80. An input 81 of the reader 80 to which the cable 79 is connected is realized as an RF input/output. The input 81 has a characteristic impedance $Z_{RF}$. The cable 79 has a characteristic impedance $Z_{cable}$. The transmission line has a characteristic impedance $Z_O$. The termination 74 also has a characteristic impedance $Z_L$. In the ideal case, the impedances at interfaces are complex conjugate to each other. For example, the impedance $Z_L$ of the termination 74 is complex conjugate to the impedance $Z_O$ of the transmission line at the end 75, 75' of the transmission line. The impedance $Z_O$ of the transmission line is complex conjugate to the impedance $Z_{cable}$ at the feeding point 73. The impedance $Z_{RF}$ is complex conjugate to the impedance $Z_{cable}$ at the input 81.

The reader 80 can be implemented as a RFID reader. The reader 80 comprises a communication interface 82. The communication interface 92 of the reader 80 can be foreseen for communication with a personal computer, Universal Serial Bus—abbreviated USB—, Inter-Integrated Circuit bus—abbreviated I2C bus—, Serial Peripheral Interface bus—abbreviated SPI bus—, a network, a controller or a middleware system.

According to the system configuration overview shown in FIG. 13, the RFID reader 80 is connected via the RF cable 79 to the transmission line 32 terminated on a load impedance 74. The transmission line is designed in a way to allow capacitive coupling between the strap 18 and itself as well as has a geometrical configuration able to achieve fully matching between the cable 79 and itself, in order to transfer all the power provided by the reader 80 to the signal line 33 and consequently to the strap 18.

A first terminal of the input 81 of the reader 80 is coupled to an input terminal of the first conducting line 33 and a second terminal of the input 81 of the reader 80 is coupled to an input terminal of the second conducting line 34. The first and the second conducting lines 33, 34 are connected in parallel to the input 81 of the reader 80.

Additionally, the second terminal of the input 81 of the reader 80 may be coupled to an input of the third conducting line 39. The first, the second and the third conducting lines 33, 34, 39 are connected in parallel to the input 81 of the reader 80.

Figure 14:
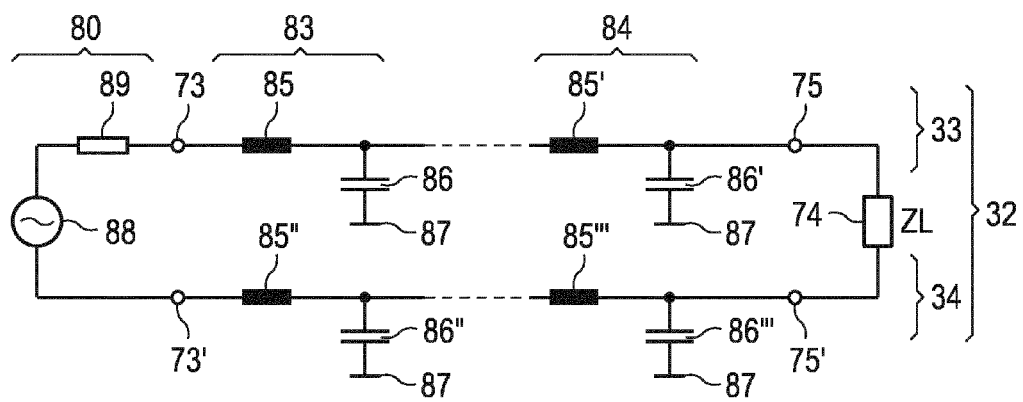
FIG. 14 shows an exemplary embodiment of a model of a signal transfer arrangement.

FIG. 14 shows an exemplary embodiment of a model of the signal transfer arrangement 32 shown above. The first conducting line 33 is modelled by a series connection of units 83, 84. Each unit 83, 84 comprises an inductor 85 and a capacitor 86. The inductors 85 of the first conducting line 33 are connected in series, whereas the capacitors 86 connect a node between the inductors 85 to a reference potential terminal 87. The second conducting line 34 also comprises several units which can be modelled as the units 83, 84 of the first conducting line 33. The end 75 of the first conducting line 33 and the end 75' of the second conducting line 34 are connected to each other via the termination 74. The reader 80 is modelled by a signal generator 88 and a resistor 89 which are series connected. The series connection of the signal generator 88 and the resistor 89 are arranged between the input terminal of the first conducting line 33 and the input terminal of the second conducting line 34. In FIG. 14, a simplified circuital model of the parallel trace transmission line is shown. The parameters of the transmission line configuration such as trace width W, inter-distance D (distance between two different traces) and dielectric substrate properties and thickness are selected in a way to allow perfect matching between the reader 80 and the conducting lines 33, 34. This will allow transferring all the power from the reader 80 to the transmission line and maximizing the coupling with the strap 18.

Figure 15:
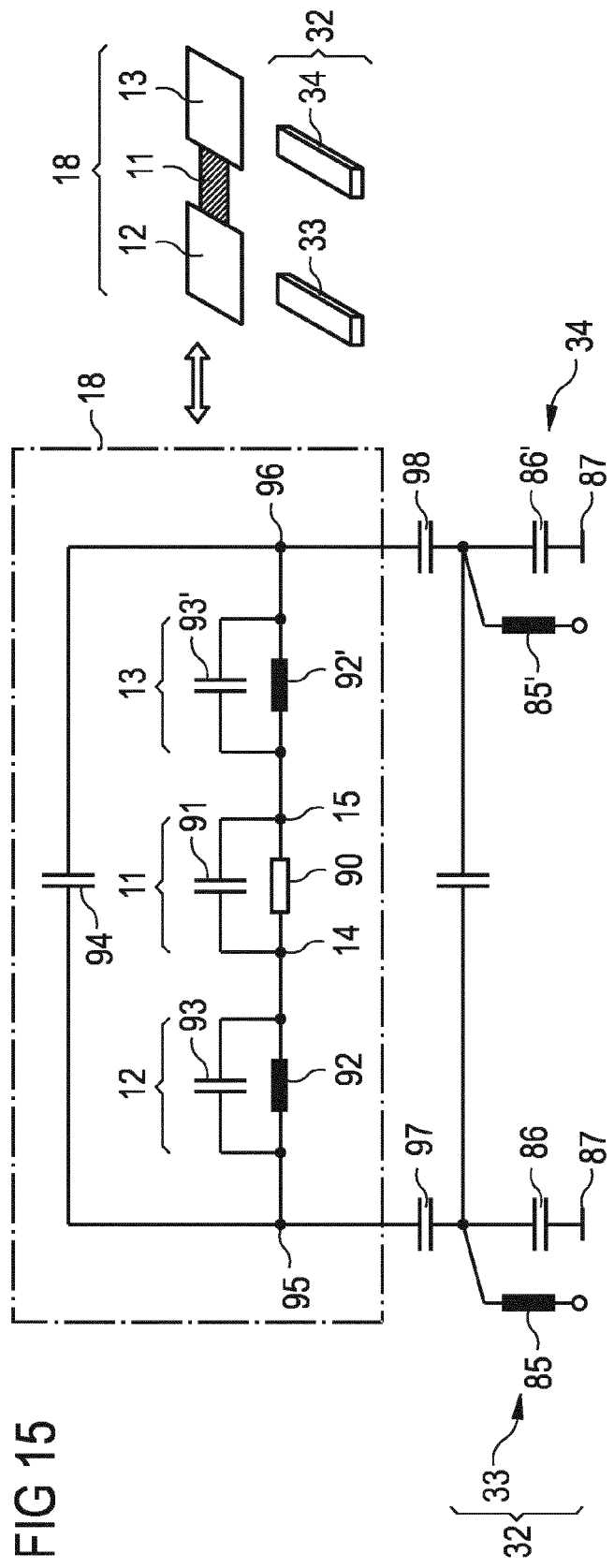
FIG. 15 shows an exemplary embodiment of an equivalent circuit of a strap and of a signal transfer arrangement.

FIG. 15 shows an exemplary embodiment of an equivalent circuit of the strap 18 and of the signal transfer arrangement 32. The integrated circuit 11 can be modelled as a parallel circuit of a resistor 90 and a capacitor 91. The capacitor 91 obtains a value of few pF, whereas the resistor 90 has a few KΩ. The first pad 12 and its connection to the integrated circuit 11, for example by the first conductive glue spot 16, can be modelled as a parallel circuit of an inductor 92 and a capacitor 93. The inductor 92 has a value of pH. A similar model can be chosen for the second pad 13. A further capacitor 94 is arranged between the outer terminals 95, 96 of the first and the second pad 12, 13. When the strap 18 is placed in proximity to the transmission line, a capacitance between the two pads 12, 13 and the two conducting lines 33, 34 is created and said capacitance allows power transfer between the transmission line and the two pads 12, 13 and consequently to the integrated circuit 11. The coupling of the first and the second pad 12, 13 to the first and second conducting line 33, 34 can be modelled by the first coupling capacitor 97 between the outer terminal 95 of the first pad 12 and the first conducting line 33. Moreover, the coupling is modelled by the second coupling capacitor 98 between the outer terminal 96 of the second pad 12 and the second conducting line 34.

Figure 16:
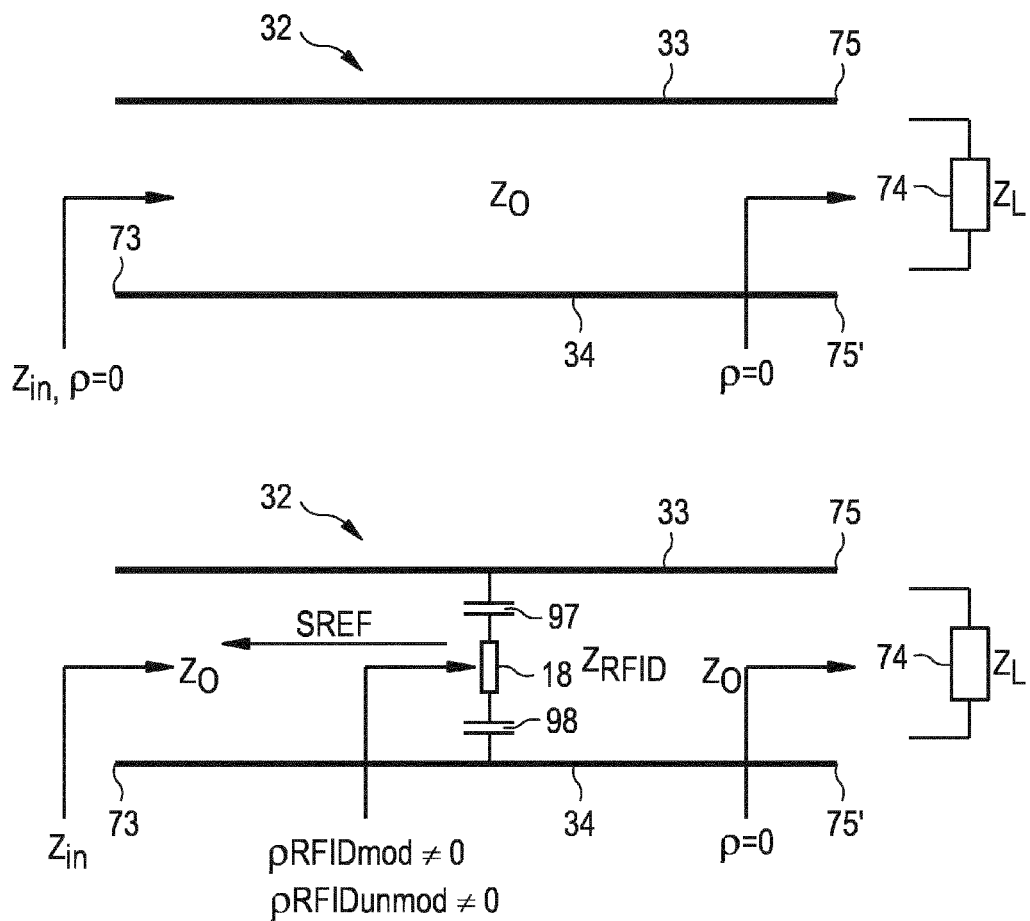
FIG. 16 shows an exemplary embodiment of a model of a signal transfer arrangement.

FIG. 16 shows an exemplary embodiment of a model of the signal transfer arrangement 32 with and without strap 18. In the upper part, the signal transfer arrangement 32 comprises a matched transmission line. The matched transmission line comprises the first and the second conducting line 33, 34 and the termination 74. In the lower part of FIG. 16, the signal transfer arrangement 32 is shown with the strap 18 which couples the first to the second conducting line 33, 34. The strap 18 causes a reflected signal SREF. The reflected signal SREF is provided to the reader 80 and is used for receiving information from the integrated circuit 11.

The information transmission system 30 uses a backscatter principle for communication by means of the transmission line with the strap 18 coupled to it. The reader 80 sends a carrier wave, abbreviated CW, at a well-defined frequency to transfer energy to the strap 18 with the integrated circuit 11 and information by modulating the carrier wave CW by using Amplitude Shift Keying modulation or Phase-Shift Keying modulation, abbreviated ASK and PSK. The strap 18 is able to receive the power transmitted by the reader 80, transform the CW in a quasi DC voltage by using a supply circuit 102, demodulate the command by a demodulator 104, perform some processing on a logic circuit 105 and answer to the request of the reader 80 by doing ASK or PSK modulation by means of a modulator 103. The modulation on the side of the integrated circuit 11 is done by switching the impedance of the integrated circuit 11 between two different states.

When the strap 18 is transferred to the transmission line and capacitive coupling occurs, at a certain point of an original fully matched transmission line a load is placed by the strap 18 that will create reflection versus the reader 80. The level of the reflected signal SREF will change between the two modulation states of the integrated circuit 11. The reader 80 will be able to decode the ASK or PSK modulated signal by demodulating the reflected signal SREF received from the transmission line.

Figure 17:
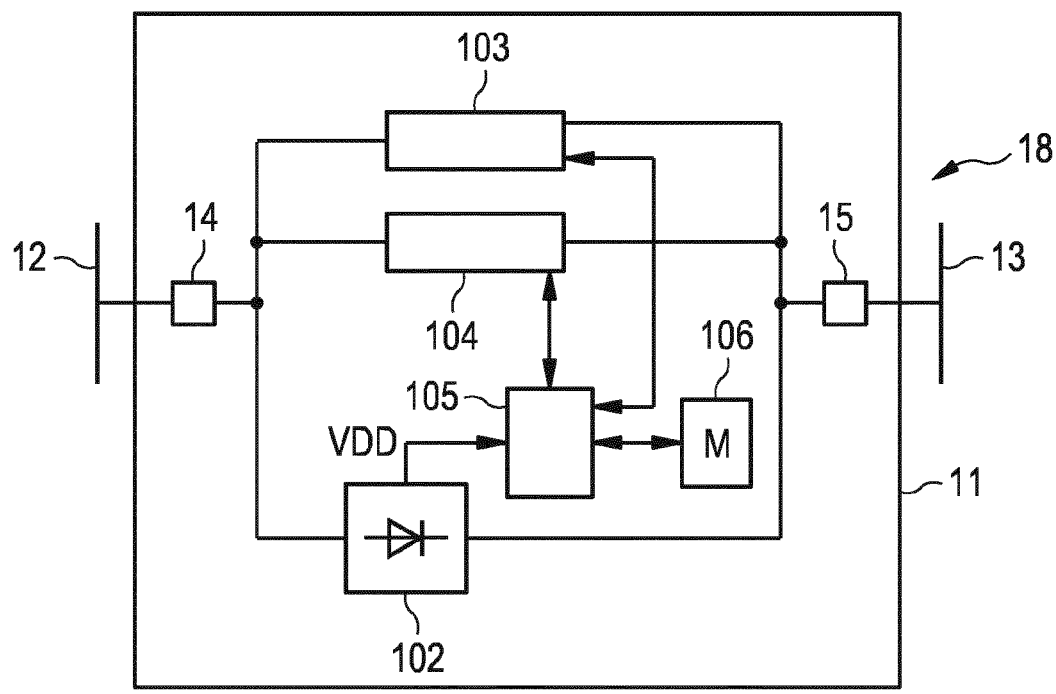
FIG. 17 shows an exemplary embodiment of an integrated circuit.

FIG. 17 shows an exemplary embodiment of the integrated circuit 11 which can be inserted in one of the above-shown information transmission systems 30. The integrated circuit 11 comprises the first and the second RF pad 14, 15 as well as the supply circuit 102 which is connected on its input side to the first and the second RF pad 14, 15. The first RF pad 14 is directly connected to the first pad 12, whereas the second RF pad 15 is directly connected to the second pad 13. The supply circuit 102 has a supply output for providing a supply voltage VDD. The supply voltage VDD is a quasi DC voltage. The supply circuit 102 comprises a rectifier. Moreover, the supply circuit 102 comprises a voltage double system. The supply circuit 102 may comprise a multi stage charge pump. The supply circuit 102 transforms the signals at the first and the second pad 12, 13 into the supply voltage VDD. Moreover, the integrated circuit 11 comprises the modulator 103 which is connected on its output side to the first and the second RF pad 14, 15. Furthermore, the integrated circuit 11 comprises the demodulator 104 which is connected on its input side to the first and the second RF pad 14, 15.

Additionally, the integrated circuit 11 comprises the logic circuit 105. The logic circuit 105 is realized as a digital signal processing unit. The logic circuit 105 is connected on its input side to the supply output of the supply circuit 102 for providing the supply voltage VDD to the logic circuit 105. The logic circuit 105 and the demodulator 104 demodulate signals provided via the first and second pad 12, 13 to the integrated circuit 11 and use the commands to perform logic calculations inside the logic circuit 105. The logic circuit 105 provides information by means of the modulator 103 and via the first and the second pad 12, 13 to the reader 80. The modulator 103 uses the ASK or PSK modulation principle. The modulator 103 obtains a first impedance value between the first and the second RF pad 14, 15 in a first modulation state and a second impedance value in a second modulation state. Moreover, the integrated circuit 11 comprises the memory 106 that is connected to the logic circuit 105. The memory 106 stores a number of the integrated circuit 11. Thus, the memory 106 comprises a read only memory segment, abbreviated ROM, or a one-time programmable memory segment, abbreviated OTP. Additionally, the memory 106 may store data received from the reader 80 via the first and the second pad 12, 13. For this purpose, the memory 106 may comprise an EEPROM segment. The integrated circuit 11 is designed as RFID integrated circuit transponder. Exactly one semiconductor body comprises the integrated circuit 11. Optionally, the integrated circuit 11 comprises a sensor such as a temperature sensor. Optionally, the integrated circuit 11 comprises an interface to another integrated circuit of the portable object 10.

Figure 18:
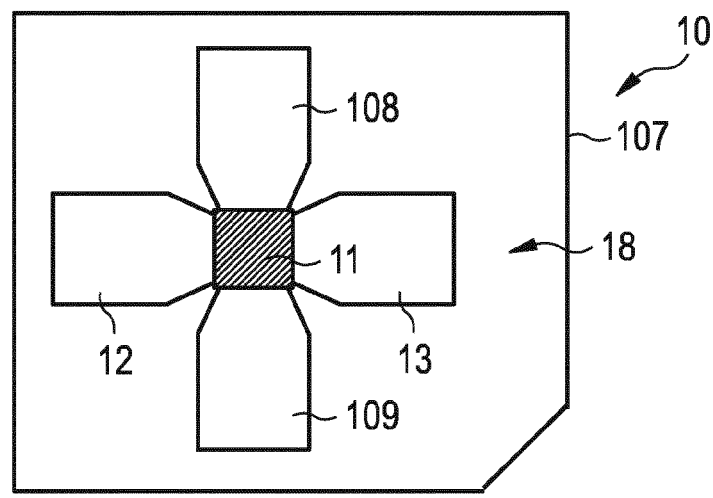
FIG. 18 shows an exemplary embodiment of a portable object.

FIG. 18 shows an additional exemplary embodiment of the portable object 10. The portable object 10 is realized as a card 107 that comprises the strap 18. The portable object 10 comprises at least a further pad 108, 109 which is connected to the integrated circuit 11. A strap 18 having three pads 12, 13, 108 can be connected with the signal transfer arrangement 32 having three conducting lines as shown for example in FIG. 4. A strap 18 having three or more pads can be connected with the signal transfer arrangement 32 having pads as shown for example in FIGS. 8A to 8C. The different pads 12, 13, 108, 109 may be used for different purposes. The first and the second pad 12, 13 are foreseen for receiving and sending data via the modulator 103 and demodulator 104. The further pads 108, 109 are designed for energy transfer to the integrated circuit 11. The further pads 108, 109 are connected to the supply circuit 102. Thus, the supply circuit 102 is not directly connected to the first and the second pad 12, 13.

The above described information transmission system 30 and method to operate can be used not only for drink and food dispenser systems 72, but in general with any identification system that use an RFID or secure element placed on a tag or SIM card or SD, micro SD portable system and which needs to be interconnected with another unit such as a personal computer or a mobile device in order to be able to dispense/provide a certain service request by the user.

Figure 19A:
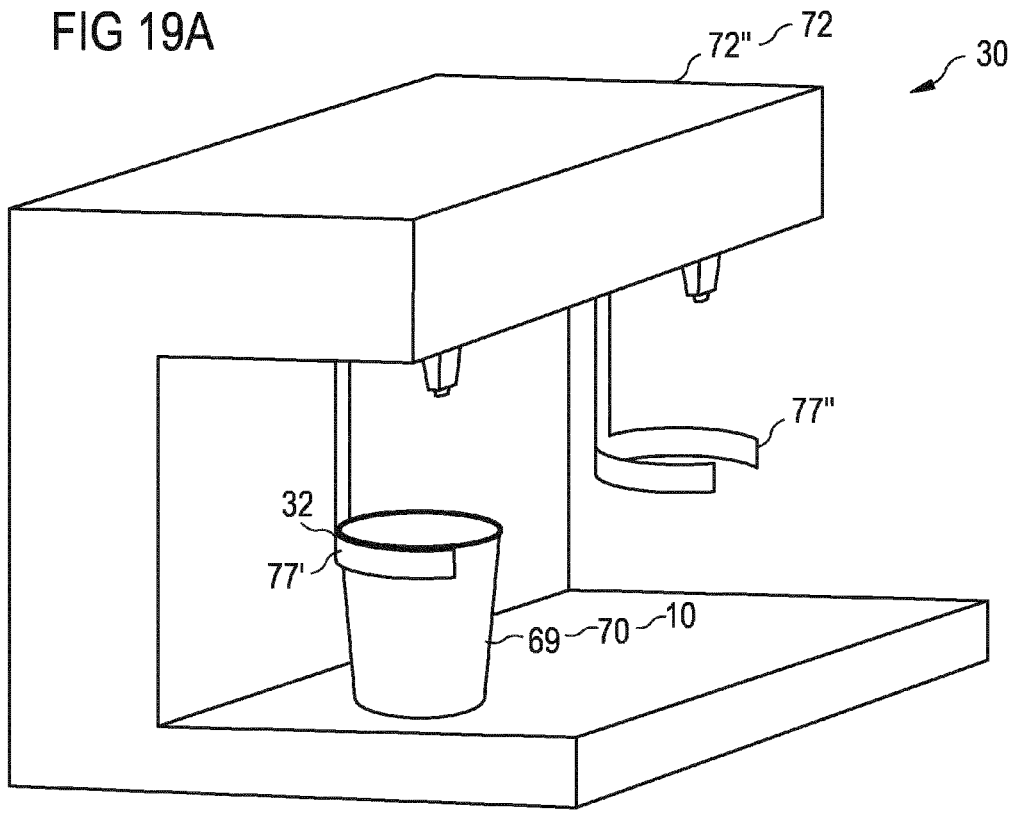
Figure 19B:
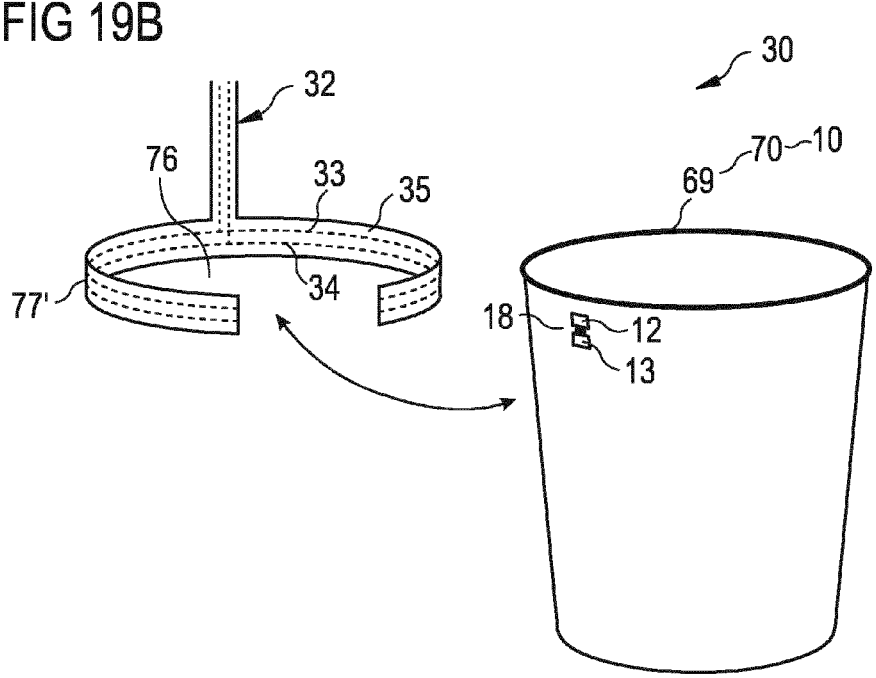

FIGS. 19A and 19B show a further exemplary embodiment of the information transmission system 30 which is a further development of the above-shown embodiments. FIG. 19A shows a schematic view of the fluid dispensing system 72 which is implemented as the coffee machine 72' or a soft drink dispenser 77'''. The portable object 10 is realized as the container 70 in form of the cup 69 comprising the strap 18. The cup 69 is realized as a coffee cup or a soft-drink cup. The fluid dispensing system 72 comprises the signal transfer arrangement 32 at the place where the cup 69 is applied by the user. The fluid dispensing system 72 identifies the cup 69 and than provides the desired drink such as soft-drink, tea, coffee or coffee-based mixture. The fluid dispensing system 72 comprises a holder 77' in which the cup 69 is inserted. The fluid dispensing system 72 comprises a further holder 77'' for inserting a further cup.

FIG. 19B shows details of the signal transfer arrangement 32 and the cup 69. The signal transfer arrangement 32 is realized in the holder 77'. Correspondingly, the further holder 77'' comprises a further signal transfer arrangement that is not shown. The holder 77' is circular. The holder 77' has the hole 76 or the opening 76. The strap 18 is at the outside of the cup 69. The strap 18 is attached to a side-wall of the cup 69. The container 70 is inserted in the hole 76 of the signal transfer arrangement 32. The holder 77' comprises a further opening at the front side.

The soft-drink dispenser 72'' can be applied in fast food restaurants, parks and resorts, where people will receive an empty cup 69 by purchasing a soft drink and they will fill the cup 69 by themselves at the fluid dispensing system 72 that is realized as a brewing machine. In order to be sure that people get their correct drink (the one purchased and not other or more), the fluid dispensing system 72 will identify the cup 69 by reading the strap 18 attached to the cup 69. The cup 69 is equipped with the strap 18. The soft-drink dispenser 72'' comprises the reader 80 embedded into it and the signal transfer arrangement 32 in form of a RF transmission line embedded into the cup holder 77' and connected to the reader 80. The cup holder 77' is a plastic part that holds the cup 69 during drink brewing. The fluid dispensing system 72 will detect the cup 69, when the cup 69 will be in contact with the cup holder 77'. The fluid dispensing system 72 will allow brewing only if the integrated circuit 11 attached to the cup 69 has been enabled at a cash point. In the same way the fluid dispensing system 72 will allow eventual refilling of the cup 69, if the integrated circuit 11 attached to it has been enabled for refilling. Said application may be used in a restaurant inside parks and/or resorts, where people may use a purchased cup 69 during all the day in several drink distributors.

FIGS. 20A and 20B show a further exemplary embodiment of the information transmission system 30 which is a further development of the above-shown embodiments. FIG. 20A shows a schematic view of the fluid dispensing system 72 which is implemented as a drug dispenser 110. The drug dispenser 110 is implemented as a pen. The portable object 10 is realized as a container 70 in the form of a cartridge 111 comprising the strap 18. The cartridge 111 is filled with a drug. The cartridge 111 is implemented as a drug cartridge. The drug dispenser 110 comprises the cartridge 111 and a dispenser unit 112. The dispenser unit 112 has the form of a tube. The cartridge 111 is implemented in the form of a cylinder. The cartridge 111 can be inserted into the dispenser unit 112 by a user. The signal transfer arrangement 32 is located at the inside of the tube such that the first and the second conducting line 33, 34 are capacitively coupled to the first and the second pad 12, 13.

Thus, the strap 18 is implemented in a medical system such as an insulin dispenser or any other dispenser. The dispenser unit 112 has mechanical and/or electronic parts. The cartridge 111 contains the drugs that have to be dispensed to a patient. An example is an insulin dispenser for a diabetic.

The drug dispenser 110 additionally comprises a needle 113 and a closing cap 114. The drug dispenser 110 is an electronic insulin dispenser. The dispenser unit 112 integrates the reader 80 into it. Moreover, the dispenser unit 112 comprises a display 115. The display 115 is fabricated as a liquid crystal display, abbreviated LCD. The display 115 displays the inserted cartridge 111 and the quantities of the drug that is to be injected. The drug cartridge 111 has a strap 18 attached to it and is inserted into the dispenser unit 112. When the cartridge 111 is inserted into the dispenser unit 112, the reader 80 embedded into the dispenser unit 112 will detect the strap 18 attached to the cartridge 111 and will identify the strap 18. The reader 80 will send information to a control circuit of the dispenser unit 112 and configure the dispenser unit 112 in order to dispense the correct amount of a drug when required. The first pad 12 and the second pad 13 are located on one circle of the wall of the cylinder of the cartridge 111. The first and the second conduction line 33, 34 that are indicated by dashed lines are located on an inner wall of the dispenser unit 112. The first and the second conduction line 33, 34 are parallel to a direction 116 during the procedure of inserting the cartridge 111 into the dispenser unit 112. Said direction 116 is parallel to the axis of the cylinder of the cartridge 11.

FIG. 20B shows an alternative orientation of the strap 18 in relation to the cylinder of the cartridge 111. The direction from the first pad 12 to the second pad 13 is parallel to the direction 116 during the procedure of inserting the cartridge 111 into the dispenser unit 112. The first and the second conduction line 33, 34 are circular. The hole 76 in the dispenser unit 112 is designed such that the first and the second pad 12, 13 are located near the first and the second conducting line 33, 34 and capacitively coupled to the first and the second conducting line 33, 34 when the cartridge 111 is inserted.

The invention claimed is:

1. An information transmission system, comprising:
a portable object comprising a strap that comprises an integrated circuit, a first pad that is mechanically and electrically connected to the integrated circuit and a second pad that is mechanically and electrically connected to the integrated circuit,
wherein the portable object is realized as a container and the strap is arranged at the outside of the container; and
a signal transfer arrangement comprising a first and a second conducting line such that selectively
either the first pad capacitively couples to the first conducting line and the second pad capacitively couples to the second conducting line, when the portable object is in vicinity of the signal transfer arrangement, or
the first and the second pad are decoupled from the first and the second conducting line, when the portable object is at a distance from the signal transfer arrangement,
wherein the signal transfer arrangement is arranged on a holder and the container is inserted into the holder such that the first and the second pad are capacitively coupled to the first and the second conducting line.

2. The information transmission system according to claim 1, wherein the first and the second conducting line are parallel to each other.

3. The information transmission system according to claim 1, wherein an extension of the first and the second pad is coordinated with an extension of the first and the second conducting line such that $$A = A1 + A2 + A3 \geq D,$$

wherein A1 is an extension of the first pad, A2 is an extension of the integrated circuit, A3 is an extension of the second pad and D is the distance of the first conducting line to the second conducting line.

4. The information transmission system according to claim 1, wherein the first and the second conducting line have a main direction and the signal transfer arrangement is designed such that the capacitive coupling of the first and the second pad to the first and the second conducting line is continued during a movement of the portable object in the main direction of the first and the second conducting line.

5. The information transmission system according to claim 1, the first and the second conducting line being arranged on a non-flat surface of the signal transfer arrangement.

6. The information transmission system according to claim 1, the signal transfer arrangement comprising:
an insulating layer attached to the first conducting line; and
at least a further pad electrically connected to the first conducting line by a via through the insulating layer.

7. The information transmission system according to claim 1, comprising a carrier body and a conducting layer, wherein the first and the second conducting line are arranged at a first surface of the carrier body and the conducting layer is fabricated on a second surface of the carrier body and forms a ground plane.

8. The information transmission system according to claim 1, wherein the signal transfer arrangement comprises a third conducting line such that the first conducting line is a signal line and is in the middle between the second and the third conducting line, wherein the second and the third conducting line are ground reference lines.

9. A portable object, comprising:
a strap that comprises an integrated circuit, a first pad that is mechanically and electrically connected to the integrated circuit and a second pad that is mechanically and electrically connected to the integrated circuit such that the portable object is designed for data transfer by capacitive coupling of the first pad to a first conducting line and of the second pad to a second conducting line, when the portable object is brought in vicinity to the first and the second conducting line,
wherein the portable object is realized as a container and the strap is arranged at the outside of the container.

10. The portable object according claim 9, the portable object being realized as an item of a group consisting of a coffee capsule, a coffee pod and a coffee pad.

11. The portable object according to claim 9, the portable object being realized as a drug cartridge.

12. The portable object according to claim 9, the portable object being realized as a card.

13. The portable object according to claim 9, wherein an area of the first pad has a larger size than an area of the integrated circuit and an area of the second pad has a larger size than the area of the integrated circuit.

14. The portable object according to claim 9, the first and the second pad being arranged to opposite edges of the integrated circuit.

15. The portable object according to claim 9, the portable object comprising a carrier which is attached on the first and the second pad such that the carrier is arranged between the first pad and the first conducting line and between the second pad and the second conducting line.

16. The portable object according to claim 9, the integrated circuit comprising:
   a supply circuit that is coupled to the first and the second pad;
   a modulator circuit that is coupled to the first and the second pad; and
   a logic circuit that is coupled to a supply output of the supply circuit for power supply and to a control input of the modulator circuit.

17. An information transmission system, comprising:
   a portable object comprising an integrated circuit, a first pad that is mechanically and electrically connected to the integrated circuit and a second pad that is mechanically and electrically connected to the integrated circuit; and
   a signal transfer arrangement comprising a first and a second conducting line such that selectively
      either the first pad capacitively couples to the first conducting line and the second pad capacitively couples to the second conducting line, when the portable object is in vicinity of the signal transfer arrangement, or
      the first and the second pad are decoupled from the first and the second conducting line, when the portable object is at a distance from the signal transfer arrangement,
   wherein an extension of the first and the second pad is coordinated with an extension of the first and the second conducting line such that $$A = A1 + A2 + A3 \geq D,$$

wherein A1 is an extension of the first pad, A2 is an extension of the integrated circuit, A3 is an extension of the second pad and D is the distance of the first conducting line to the second conducting line.

18. A portable object, comprising:
   an integrated circuit, a first pad that is mechanically and electrically connected to the integrated circuit, and a second pad that is mechanically and electrically connected to the integrated circuit such that the portable object is designed for data transfer by capacitive coupling of the first pad to a first conducting line and of the second pad to a second conducting line, when the portable object is brought in vicinity to the first and the second conducting line,
   wherein the portable object is free of an antenna.

* * * * *